(12) United States Patent
Cunningham et al.

(10) Patent No.: US 8,953,159 B2
(45) Date of Patent: Feb. 10, 2015

(54) SURFACE ENHANCED RAMAN SPECTROSCOPY NANODOME BIOSENSORS AND METHODS OF MANUFACTURING THE SAME

(75) Inventors: Brian T. Cunningham, Champaign, IL (US); Charles J. Choi, Bethesda, MD (US); Alysia R. Watkins, East Providence, RI (US)

(73) Assignees: The Board of Trustees of the University of Illinois, Urbana, IL (US); X-Body, Inc., Waltham, MA (US)

( * ) Notice: Subject to any disclaimer, the term of this patent is extended or adjusted under 35 U.S.C. 154(b) by 123 days.

(21) Appl. No.: 13/438,950

(22) Filed: Apr. 4, 2012

(65) Prior Publication Data

US 2012/0309080 A1 Dec. 6, 2012

Related U.S. Application Data

(63) Continuation-in-part of application No. 12/586,516, filed on Sep. 22, 2009, now Pat. No. 8,384,892.

(60) Provisional application No. 61/575,391, filed on Aug. 18, 2011, provisional application No. 61/518,124, filed on Apr. 29, 2011, provisional application No. 61/195,133, filed on Oct. 3, 2008.

(51) Int. Cl.
*G01J 3/44* (2006.01)
*G02B 1/00* (2006.01)
*G01N 21/65* (2006.01)

(52) U.S. Cl.
CPC .............. *G02B 1/005* (2013.01); *G01N 21/658* (2013.01)
USPC ....................................................... 356/301

(58) Field of Classification Search
USPC .............................................. 356/301, 72–73
See application file for complete search history.

(56) References Cited

U.S. PATENT DOCUMENTS

| | | | |
|---|---|---|---|
| 5,527,712 A | 6/1996 | Sheehy | 436/525 |
| 6,990,259 B2 | 1/2006 | Cunningham | 385/12 |
| 7,094,595 B2 | 8/2006 | Cunningham et al. | 435/287.2 |
| 7,118,710 B2 | 10/2006 | Cunningham | 422/82.09 |
| 7,148,964 B2 | 12/2006 | Cunningham et al. | 356/326 |
| 7,289,690 B2 | 10/2007 | Li et al. | 385/12 |
| 7,314,751 B2 | 1/2008 | Kelleher et al. | 435/288.7 |
| 7,531,786 B2 | 5/2009 | Cunningham et al. | 250/214.1 |

(Continued)

OTHER PUBLICATIONS

Campion A., Kambhampati, P., *Surface-enhanced Raman scattering*, Chemical Society Reviews, 27, (4), pp. 241-250,1998.

(Continued)

*Primary Examiner* — Abdullahi Nur
(74) *Attorney, Agent, or Firm* — McDonnell Boehnen Hulbert & Berghoff LLP

(57) ABSTRACT

Tubing such as clear plastic disposable tubing or glass tubing includes a photonic sensor formed in or placed within the tubing. The photonic sensors can take the form of photonic crystal sensors, distributed feedback laser sensors, and surface enhanced Raman spectroscopy (SERS) sensors, including photonic crystal enhanced SERS sensors. Detection arrangements for the sensors are described. The invention has many applications including tubing used in hospital care (e.g., urinary catheters, intravenous fluid delivery tubing, tubing used in dialysis, e.g. heparin lines or blood tubing sets), food manufacturing, pharmaceutical manufacturing, water quality monitoring, and environmental monitoring.

16 Claims, 22 Drawing Sheets

(56) References Cited

U.S. PATENT DOCUMENTS

| | | | |
|---|---|---|---|
| 7,737,392 B2 | 6/2010 | Cunningham et al. | 250/214.1 |
| 7,875,434 B2 | 1/2011 | Lin et al. | 435/7.2 |
| 2002/0127565 A1 | 9/2002 | Cunningham et al. | 435/6 |
| 2002/0182716 A1 | 12/2002 | Weisbuch | 435/287.2 |
| 2003/0027327 A1 | 2/2003 | Cunningham et al. | 435/287.2 |
| 2003/0059855 A1 | 3/2003 | Cunningham et al. | 435/7.9 |
| 2004/0125449 A1* | 7/2004 | Sales | 359/486 |
| 2004/0180379 A1 | 9/2004 | Van Duyne et al. | 435/7.1 |
| 2006/0056463 A1 | 3/2006 | Wang | 372/3 |
| 2007/0009380 A1 | 1/2007 | Cunningham | 4/422 |
| 2007/0009968 A1 | 1/2007 | Cunningham et al. | 435/7.9 |
| 2008/0094621 A1* | 4/2008 | Li et al. | 356/301 |
| 2008/0220535 A1* | 9/2008 | LeBoeuf et al. | 436/164 |
| 2008/0246961 A1 | 10/2008 | Zhang et al. | |
| 2009/0051913 A1 | 2/2009 | Sugita | 356/246 |
| 2009/0118605 A1 | 5/2009 | Van Duyne et al. | 600/385 |
| 2009/0179637 A1 | 7/2009 | Cunningham et al. | 324/304 |
| 2010/0085566 A1 | 4/2010 | Cunningham | 356/301 |
| 2010/0087723 A1 | 4/2010 | Van Duyne et al. | 600/365 |
| 2011/0019186 A1* | 1/2011 | Himmelhaus et al. | 356/317 |
| 2012/0113419 A1 | 5/2012 | Wang | 356/301 |

OTHER PUBLICATIONS

Gopinath, A. et al., *Plasmonic Nanogalaxies: Multiscale Aperiodic Arrays for Surface-Enhanced Raman Sensing*, Nano Letters, 9, (11), pp. 3922-3929, 2009.
Radomska, A. et al., *Bioanalytical System for Control of Hemodialysis Treatment Based on Potentiometric Biosensors for Urea and Creatinine*, Analytica Chimica Acta, 523, pp. 193-200, 2004.
Yalcin, A. et al., *Optical sensing of biomolecules using microring resonators*, Ieee Journal of Selected Topics in Quantum Electronics, 12, pp. 148-155, Jan.-Feb. 2006.
Baca, A.J. et al., *Molded plasmonic crystals for detecting and spatially imaging surface bound species by surface-enhanced Raman scattering*, Applied Physics Letters, 94 (24) 2009.
Haes, A.J. et al., *Plasmonic materials for surface-enhanced sensing and spectroscopy*, MRS Bulletin, 30 (5), pp. 368-375, 2005.
Lin, B. et al., *A label-free biosensor-based cell attachment assay for characterization of cell surface molecules*, Sensors and Actuators B, 114, pp. 559-561, 2006.
Premanide, B. et al., *A novel, low power biosensor for real time monitoring of creatinine and urea in peritoneal dialysis*, Sensors and Actuators B, vol. 120, pp. 732-735, 2006.
Serra, B. et al., *Lectin-modified piezoelectric biosensors for bacteria recognition and quantification*, Analytical Bioanalytical Chemistry, vol. 391, pp. 1853-1860, 2008.
Cunningham, B.T. et al., *Label-free detection of biomolecular interactions: applications in proteomics and drug discovery*, Expert Review of Proteomics, vol. 3, pp. 271-281, 2006.
Cunningham, B.T. et al., *A plastic colorimetric resonant optical biosensor for multiparallel detection of label-free biochemical interactions*, Sensors and Actuators B-Chemical, vol. 85, pp. 219-226, Jul. 25, 2002.
Cunningham, B.T. et al., *Enhancing the surface sensitivity of colorimetric resonant optical biosensors*, Sensors and Actuators B, vol. 87, pp. 365-370, 2002.
Cunningham, B.T. et al., *Colorimetric resonant reflection as a direct biochemical assay technique*, Sensors and Actuators B, vol. 81, pp. 316-328, 2002.
Cunningham, B T. et al., *Label-Free Assays on the BIND System*, Journal of Bimolecular Screening, vol. 9, pp. 481-490, 2004.
Tisher, C.G. et al., *Morbidity and mortality of renal dialysis; an NIH conference statement* Annals of Internal Medicine, vol. 121, pp. 62-70, 1994.
Choi, C.J. et al., *Surface-enhanced Raman nanodomes*, Nanotechnology, vol. 21, p. 415301, 2010.
Choi, C.J. et al., *Label-Free Photonic Crystal Biosensor Integrated Microfluidic Chip for Determination of Kinetic Reaction Rate Constants*, Ieee Sensors Journal, vol. 9 (12), pp. 1697-1704, 2009.
Choi, C.J. et al, *A 96-well microplate incorporating a replica molded microfluidic network integrated with photonic crystal biosensors for high throughput kinetic biomolecular interaction analysis*, Lab on a Chip, 7 (5), pp. 550-556, 2007.
Choi, C.J. et al., *Single-step fabrication and characterization of photonic crystal biosensors with polymer microfluidic channels*, Lab on a Chip, 6 (10), pp. 1373-1380, 2006.
Choi, C.J. et al., *Biochemical sensor tubing for point-of-care monitoring of intravenous drugs and metabololite*, Lab on a Chip, 2011.
Ortiz, C. et al., *Identification of insulin variants using Raman spectroscopy*, Analytical Biochemistry, vol. 32, pp. 245-252, 2004.
Eddy C.V. et al., *Near-Infrared Spectroscopy for Measuring Urea in Hemodialysis Fluids*, Automation and Anatytical Techniques, vol. 47, pp. 1279-1286, 2001.
Chao, C.Y. et al., *Polymer microring resonators for biochemical sensing applications*, Ieee Journal of Selected Topics in Quantum Electronics, vol. 12, pp. 134-142, Jan.-Feb. 2006.
Haynes, C.L. et al., *Nanosphere lithography; A versatile nanofabrication tool for studies of size-dependent nanoparticle optics*, Journal of Physical Chemistry B, vol. 105 (24), pp. 5599-5611, 2001.
Huang, C. P. et al., *A highly sensitive for urea detection by using CdSe/ZnS core-shell quantum dots.*, Biosens Bioelectron, vol. 22 (8), pp. 1835-1838, Mar. 15, 2007.
CDC, *Guidelines for the prevention of intravascular catheter-related infection*, MMWR, vol. 51, p. 40937, 2002.
Atha, D.H., Gaigalas, A.K., Reipa, V., *Structural analysis of heparin by raman spectroscopy*, J Pharm Sci, vol. 85 (1), pp. 52-56, Jan. 1996.
Bates, D.W. et al., *The costs of adverse drug events in hospitalized patients*, Adverse Drug Events Prevetion Study Group, JAMA, vol. 277 (4), pp. 307-311, Jan. 22-29, 1997.
Jeanmaire., D.L, et al., *Surface Raman Spectroelectrochemistry .1. Heterocyclic, Aromatic, and Aliphatic-Amines Adsorbed on Anodized Silver Electrode*, Journal of Electroanalytical Chemistry, vol. 84 (1), p. 40928, 1977.
Grubisha D.S., et al., *Femtomolar detection of prostate-specific antigen: an immunoassay based on surface-enhanced Raman scattering and immunogold labels*, Anal Chem, vol. 75 (21), pp. 5936-5943, Nov. 1, 2003.
Vollmer, F. et al., *Protein detection by optical shift of a resonant microcavity*, Applied Physics Letters, vol. 80, pp. 4057-4059, May 27, 2002.
Yang, F.Y. et al., *Optically tuned resonant optical reflectance filter*, Applied Physics Letters, vol. 92 (9), 2008.
Slavik, G.J. et al., *A replica molding technique for producing fibrous chitosan scaffolds for cartilage engineering*, Journal of Materials Chemistry, vol. 17 (38), pp. 4095-4101, 2007.
Liu, G.L. et al., *Nanowell surface enhanced Raman scattering arrays fabricated by soft-lithography for label-free biomolecular detections in integrated microfluidics*, Applied Physics Letters, vol. 87 (7), 2005.
Wu, H.Y. et al., *Plasmonic coupling of SiO2-Ag "post-cap" nanostructures and silver film for surface enhanced Raman scattering*, Applied Physics Letters, vol. 98, pp. 3555342-3555344, 2011.
Block, I.D. et al., *A sensitivity model for predicting photonic crystal biosensor performance*, IEEE Sensors Journal, vol. 8, pp. 274-280, Mar. 2008.
Hatcher, I. et al., *An intravenous medication safety system: preventing high-risk medication errors at the point of care*, J Nurs Adm, vol. 34 (10), pp. 437-439, Oct. 2004.
White I.M., Fan, X., *On the performance quantification of resonant refractive index sensors.*, Opt Express, vol. 16 (2), pp. 1020-1028, Jan. 21, 2008.
White, I.M., et al., *Liquid-core optical ring-resonator sensors*, Optics Letters, vol. 31, pp. 1319-1321, 2006.
White, I.M. et al., *SERS-based detection in an optofluidic ring resonator platform*, Optics Express, vol. 15 (25), pp. 17433-17442 (2007).
Block, I.D., et al., *A detection instrument for enhanced-fluorecence and label-free imaging on photonic crystal surfaces*, Opt Express, vol. 17 (15), pp. 13222-13235, Jul. 20, 2009.

(56) References Cited

OTHER PUBLICATIONS

Eskew, J.A. et al., *Using innovative technologies to set new safety standards for the infusion of intravenous medications*, Hospital Pharmacist, vol. 37, pp. 1179-1189, 2002.
Rogers, J.A. et al., *Distributed feedback ridge waveguide lasers fabricated by nanoscale printing and molding on nonplanar substrates*, Applied Physics Letters, vol. 74, pp. 3257-3259, May 31, 1999.
Barr, H. et al., *Photodiagnosis using Raman and surface enhanced Raman scattering of bodily fluids*, Photodiagnosis and Photodynamic Therapy, vol. 2, pp. 223-233, 2005.
Zhao J., et al., *Automated autofluorescence background subtraction algorithm for biomedical Raman spectroscopy*, Appl Spectrosc, vol. 61 (11), pp. 1225-1232, Nov. 2007.
Kneipp, K. et al., *Single molecule detection using surface-enhanced Raman scattering (SERS)*, Physical Review Letters, vol. 78 (9), pp. 1667-1670, 1997.
Ueno, K. et al., *Clusters of Closely SPaced Gold Nanoparticles as a Source of Two Photon Photoluminescence at Visible Wavelengths*, Advanced Materials, vol. 20, pp. 26-30, 2008.
Wilson, K., Sullivan, M., *Preventing medication errors with smart infusion technology.*, Am J Health Syst Pharm, vol. 61 (2), pp. 177-183, Jan. 15, 2004.
Biggs, K. B. et al., *Surface-enhanced Raman spectroscopy of benzenethiol adsorbed from the gas phase onto silver film over nanosphere surfaces: determination of the sticking probability and detection limit time*, J Phys Chem A, vol. 113 (16), pp. 4581-4586, Apr. 23, 2009.
Della, Ciana L. et al., *Reliable biosensor for continuous monitoring of urea during dialysis*, Clin Chem, vol. 42 (7), pp. 1079-1085, Jul. 1996.
Gunnarsson, L. et al., *Interparticle coupling effects in nanofabricated substrates for surface-enhanced Raman scattering*, Applied Physics Letters, vol. 78 (6), pp. 802-804, 2001.
Chan, L.L., et al., *A label-free photonic crystal biosensor imaging method for detection of cancer cell cytotoxicity and proliferation*, Apoptosis, vol. 12 (6), pp. 1061-1068, Jun. 2007.
Chan, L.L. et al., *Label-free imaging of cancer cells using photonic crystal biosensors and application to cytotoxicity screening of a natural compound library*, Sensors and Actuators B, 132, pp. 428-425, 2008.
Dick, L.A. et al., *Metal film over nanosphere (MFON) electrodes for surface-enhanced Raman spectroscopy (SERS): Improvements in surface nanostructure stability and suppression of irreversible loss*, Journal of Physical Chemistry B, vol. 106 (4), pp. 853-860, 2002.
Cooper, M.A., *Optical Biosensors in Drug Discovery*, Nature Reviews, vol. 1, pp. 5125-5528, Jul. 2002.
Pineda, M.F et al., *Rapid label-free selective detection of porcine rotavirus using photonic crystal biosensors for groundwater monitoring*, IEEE Sensors Journal, 2009.
Fleischmann, M. et al., *Raman-Spectra of Pyridine Adsorbed at a Silver Electrode*, Chemical Physics Letters, vol. 26 (2), pp. 163-166, 1974.
Goetz, M.J. Jr, et al., *Application of a multivariate technique to Raman spectra for quantification of body chemicals*, IEEE Trans Biomed Eng, vol. 42 (7), Jul. 1995.
Loncar, M. et al., *Photonic crystal laser sources for chemical detection*, Applied Physics Letters, vol. 82, pps. 4648-4650, Jun. 30, 2003.
Lu, M. et al., *Vertically emitting dye-doped polymer laser in the green (lambda=536 nm) with a second order distributed feedback grating fabricated by replica molding* Optics Communication, vol. 281, pp. 3159-3162, 2008.
Lu, M. et al, *Microcavity plasma devices and arrays fabricated by plastic-based replica molding*, Journal of Microelectromechanical Systems, vol. 16 (6), pp. 1397-1402, 2007.
Lu, M. et at, *Label-free biosensor incorporating a replica-molded, vertically emitting distributed feedback laser*, Applied Physics Letter, vol. 92, pp. 261502-261504, 2008.
Lu, M. et al., *Plastic distributed feedback laser biosensor*, Applied Physics Letters, vol. 93, p. 111113, 2008.
Moskovits, M., *Surface-Enhanced Spectroscopy*, Reviews of Modern Physics, vol. 57 (3), pp. 783-826, 1985.
Felidj, N. et al., *Optimized surface-enhanced Raman scattering on gold nanoparticle arrays*, Applied Physics Letters, vol. 82 (18), pp. 3095-3097, 2003.
Félidj, N., et al., *Gold particle interaction in regular arrays probed by surface-enhanced Raman scattering*, J Chem Phys, vol. 120 (15), pp. 7141-7146, Apr. 15, 2004.
Ganesh N, et al., *Enhanced fluorescence emission from quantum dots on a photonic crystal surface*, Nat Nanotechnol, vol. 2 (8), pp. 515-520, Aug. 2007.
Hanumegowda, N.M. et al., *Refractometric sensors based on microsphere resonators*, Applied Physics Letters, vol. 87, Nov. 14, 2005.
Pieczonka N.P., Aroca, R.F., *Single molecule analysis by surfaced-enhanced Raman scattering*, Chem Soy Rev, vol. 37 (5), pp. 946-954, May 2008.
Yu N.T., et al., *Raman spectroscopy and the conformation of insulin and proinsulin*, J Mol Biol, vol. 70 (1), pp. 117-132, Sep. 14, 1972.
Neumann O., et al., *Direct optical detection of aptamer conformational changes induced by target molecules*, Anal Chem, vol. 81 (24), pp. 10002-10006, Dec. 15, 2009.
Primera-Pedrozo O.M. et al., *Nanotechnology-based detection of explosives and biological agents simulants*, IEEE Sensors Journal, vol. 8, pp. 41035, 963-973, 2008.
Mathias P.C., et al., *Application of photonic crystal enhanced fluorescence to a cytokine immunoassay*, Anal Chem, vol. 80 (23), 9013-20, Dec. 1, 2008.
Liao, P.F. et al., *Surface-Enhanced Raman-Scattering from Microlithographic Silver Particle Surfaces*, Chemical Physics Letters, vol. 82 (2), pp. 355-359, 1981.
Etchegoin, P.G., Le Ru E.C., *A perspective on single molecule SERS: current status and future challenges*, Phys Chem Chem Phys, vol. 10, (40), pp. 607989, Oct. 28, 2008.
Stiles, P.L. et al., *Surface-Enhanced Raman Spectroscop*, Annual Review of Amalytical Chemistry, vol. 1, pp. 601-826, 2008.
Shaw, R.A. et al., *Quantitation of protein, creatinine, and urea in urine by near-infrared spectroscopy*, Clin Biochem, vol. 29 (1), pp. 41232, Feb. 1996.
Kazarinov, R.F. et al., *2Nd-Order Distributed Feedback Lasers with Mode Selection Provided by 1St-Order Radiation Losses*, IEEE Journal of Quantum Electronics, vol. 21, pp. 144-150, 1985.
Jarvis, R.F., Goodacre, R., *Discrimination of bacteria using surface-enhanced Raman spectroccopy*, Anal Chem vol. 76 (1), pp. 40-47, Jan. 1, 2004.
Kaushal, R. et al., *Medication errors and adverse drug events in pediatric inpatients*, JAMA, vol. 285 (16), pp. 2114-2120, Apr. 25, 2001.
Stosch, R., et al., *Surface-enhanced Raman scattering based approach for quantitative determination of creatinine in human serum*, Anal Chem, vol. 77 (22), pp. 7386-7392, Nov. 15, 2005.
Balasubramanian, S. et al., *Lytic phage as a specific and selective probe for detection of Staphylococcus aureus—A surface plasmon resonance spectroscopic study*, Biosens Bioelectron, vol. 22 (6), pp. 948-955, Jan. 15, 2007.
Carrigan, S.D., et al., *Toward resolving the challenges of sepsis diagnosis*, Clin Chem, vol. 50 (8), pp. 1301-1314, Aug. 2004.
Kim, S.M., et al., *Coupling discrete metal nanoparticles to photonic crystal surface resonant modes and application to Raman spectroscopy*, Opt Express, vol. 18 (5), pp. 4300-4309, Mar. 1, 2010.
Kim, SM et al., *Photonic crystals with SiO2—Ag "post-cap" nanostructure coatings for surface enhanced Raman spectroscopy*, Applied Physics Letters, vol. 93, 2008.
Wang, S.S., Magnusson, R., *Theory and applications of guided-mode resonance filters*, Appl Opt, vol. 32 (14), pp. 2606-2613, May 10, 1993.
Shanmukh, S. et al., *Rapid and sensitive detection of respiratory virus molecular signatures using a silver nanorod array SERS substrate*, Nano Lett, vol. 6 (11), pp. 2630-2636, Nov. 2006.
Thurman, S., et al., *Intravenous medication safety systems help prevent harm and career ending mistakes, Extensive nursing input helps design easy-to-use system that intercepts critical errors*, J Nurs Adm, vol. 34 Suppl, p. 40943, Dec. 2004.

(56) References Cited

OTHER PUBLICATIONS

Nie, S., Emory S.R., *Probing Single Molecules and Single Nanoparticles by Surface-Enhanced Raman Scattering*, Science, vol. 275 (5303), pp. 1102-1106, Feb. 21, 1997.

Golpher, T. et al., *National Kidney Foundation, DOQI—Dialysis outcome quality Initiative. Clinical practice guidelines for peritoneal dialysis adequacy*, American Journal of Kidney Disease, vol. 30, S67-S136, 1997.

Jönsson, U. et al., *Real-time biospecific interaction analysis using surface plasmon resonance and a sensor chip technology*, Biotechniques, vol. 11 (5), pp. 620-627, Nov. 1991.

Drachev, V.P. et al., *Emicontinuous silver films for protein sensing with SERS*, Proceedings of the SPIE: Plasmonics: Metallic Nanostructures and Their Optical Properties, 5521, pp. 75-81, 2003.

Lin, V.S., et al., *A porous silicon-based optical interferometric biosensor*, Science, 278, 5339, pp. 840-843, Oct. 31, 1997.

Fang, W. et al., *Detection of chemical species using ultraviolet microdisk lasers*, Applied Physics Letters, vol. 85, pp. 3666-3668, Oct. 25, 2004.

Premasiri, W.R. et al., *Urine analysis by laser Raman Spectroscopy*, Lasers in Surgery and Medicine, vol. 28, 330-334, 2001.

Zhang, W. et al., *High sensitivity photonic crystal biosensor incorporating nanorod structures for enhanced surface area*, Sensor and Actuators B, vol. 131, pp. 279-284, 2008.

Zhang, W et al., *Deposited nanorod films for biosensor applications*, J Vac Sci Technol A, vol. 28, pp. 996-1001, 2010.

Zhang, W. et al., *Enhanced fluorescence on a photonic crystal surface incorporating nanorod structures*, Small, vol. 4 (12), pp. 2199-2203, Dec. 2008.

Xie, X., et al., *Determination of urea in serum by a fiber-optic fluorescence biosensors*, Talanta, vol. 38 (100), pp. 1197-1200, Oct. 1991.

Lu, Y. et al., *Nanophotonic crescent moon structures with sharp edge for ultrasensitive biomolecular detection by local electromagnetic field enhancement effect*, Nano Lett, vol. 5 (1), pp. 119-124, Jan. 2005.

Oki, Y. et al., *Long lifetime and high repetition rate operation from distributed feedback plastic waveguide dye lasers*, Optics Communication, vol. 214, pp. 277-283, 2002.

Zhao, V.P. et al., *Polarized surface enhanced Raman and absorbance spectra of aligned silver nanorod arrays*; J Phys Chem B, vol. 110 (7), pp. 3153-3157, Feb. 23, 2006.

Cao, Y.C., et al., *Nanoparticles with Raman spectroscopic fingerprints for DNA and RNA detection*, Science, vol. 297, pp. 5586, 1536-40, Aug. 30, 2002.

Seifert, Jansen and Farr, Eds., *Catheter Related Infections*, Chap. 2, pp. 31-57, Marcel Dekker Inc., 1997.

Narayanaswamy and Wolfbeis, Eds., *Optical Sensors*, Chap. 7, pp. 145-172, Springer, 2004.

Cunningham, Alice, Ed., *Introduction to Bioanalytical Sensors*, pp. 45-54, 284-285, 288, 290, John Wiley & Sons, 1998.

* cited by examiner

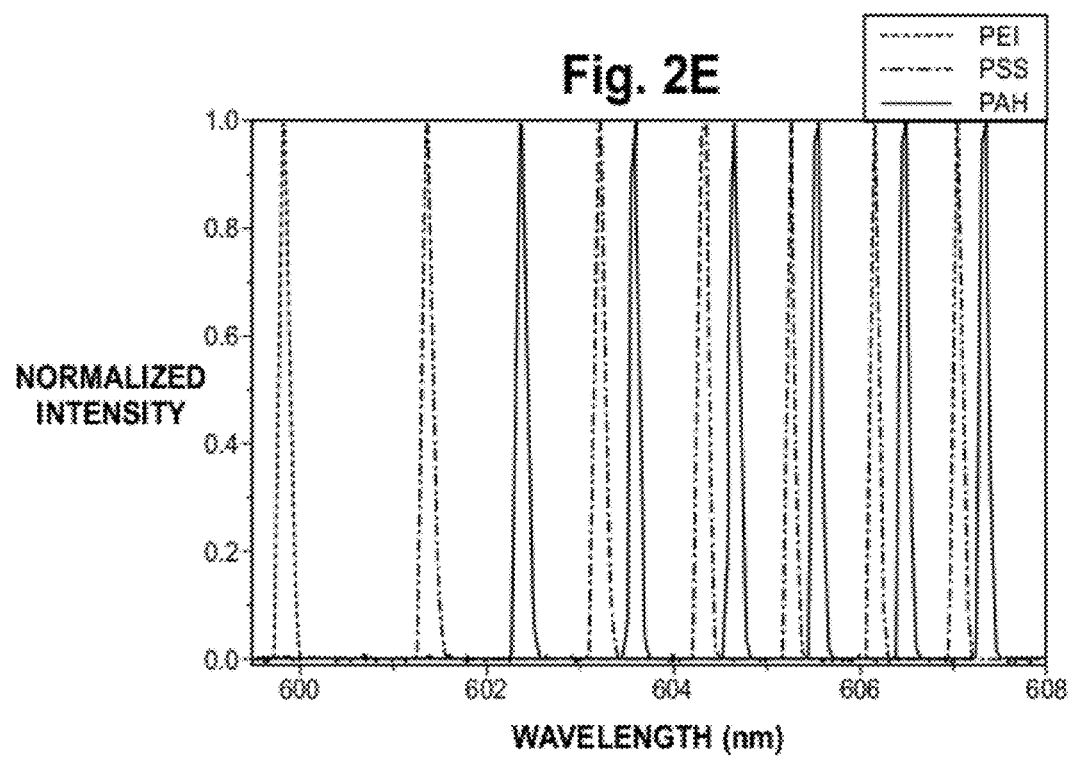
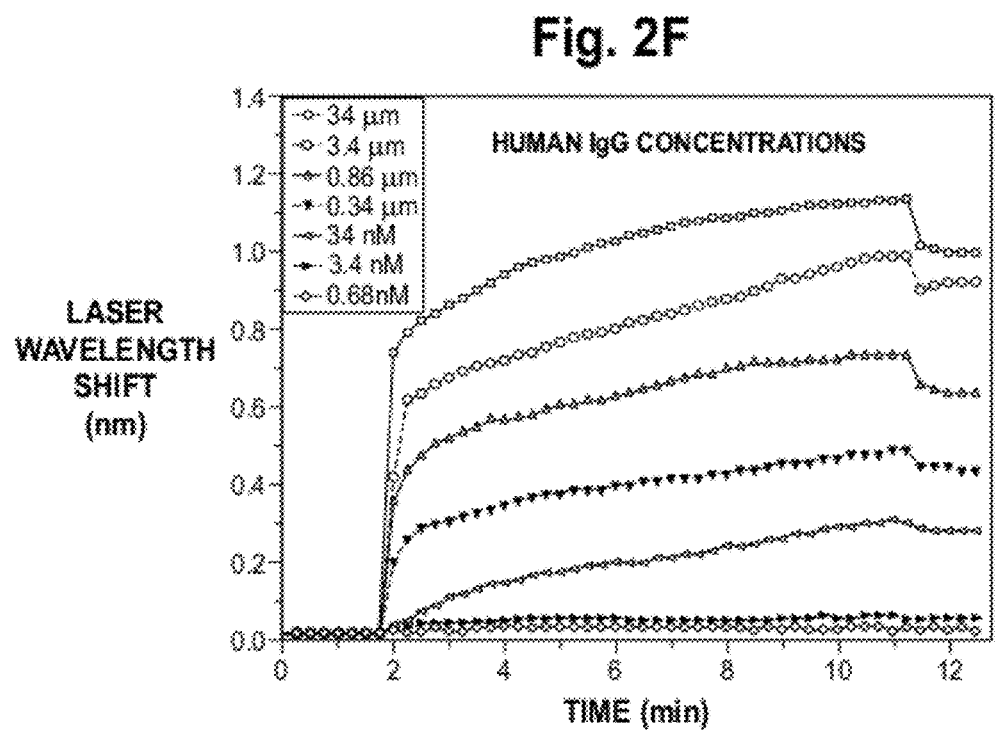

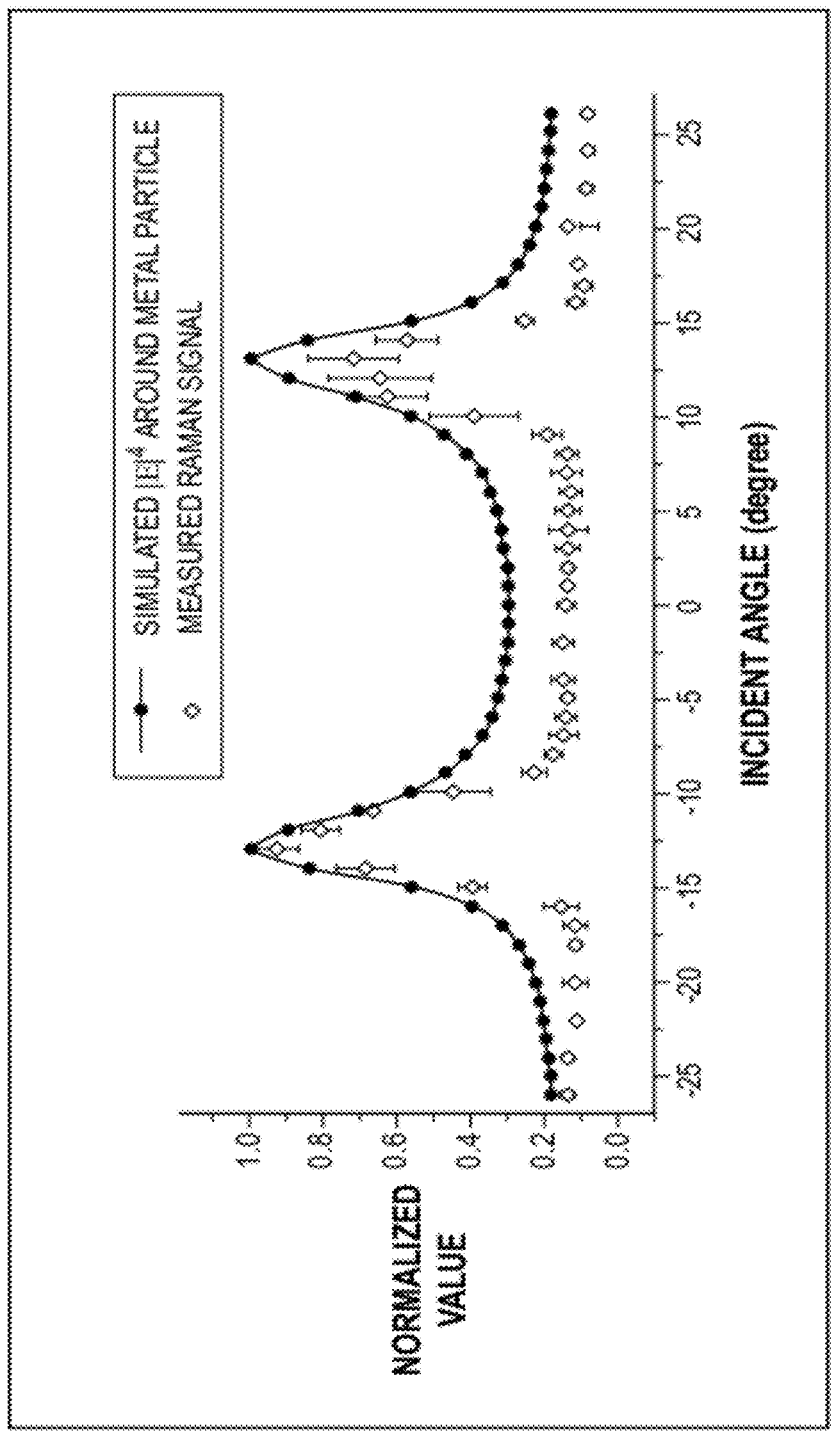

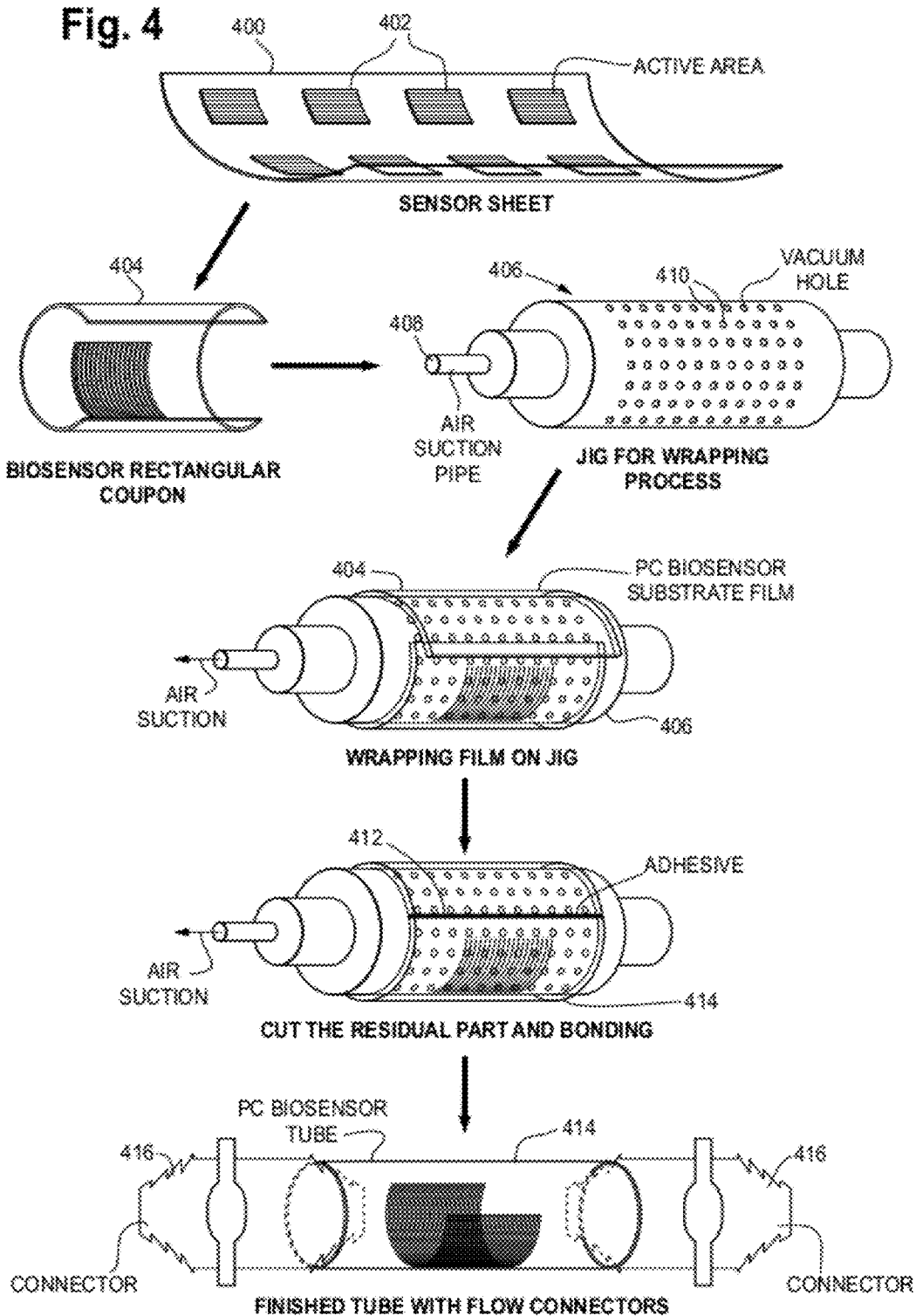

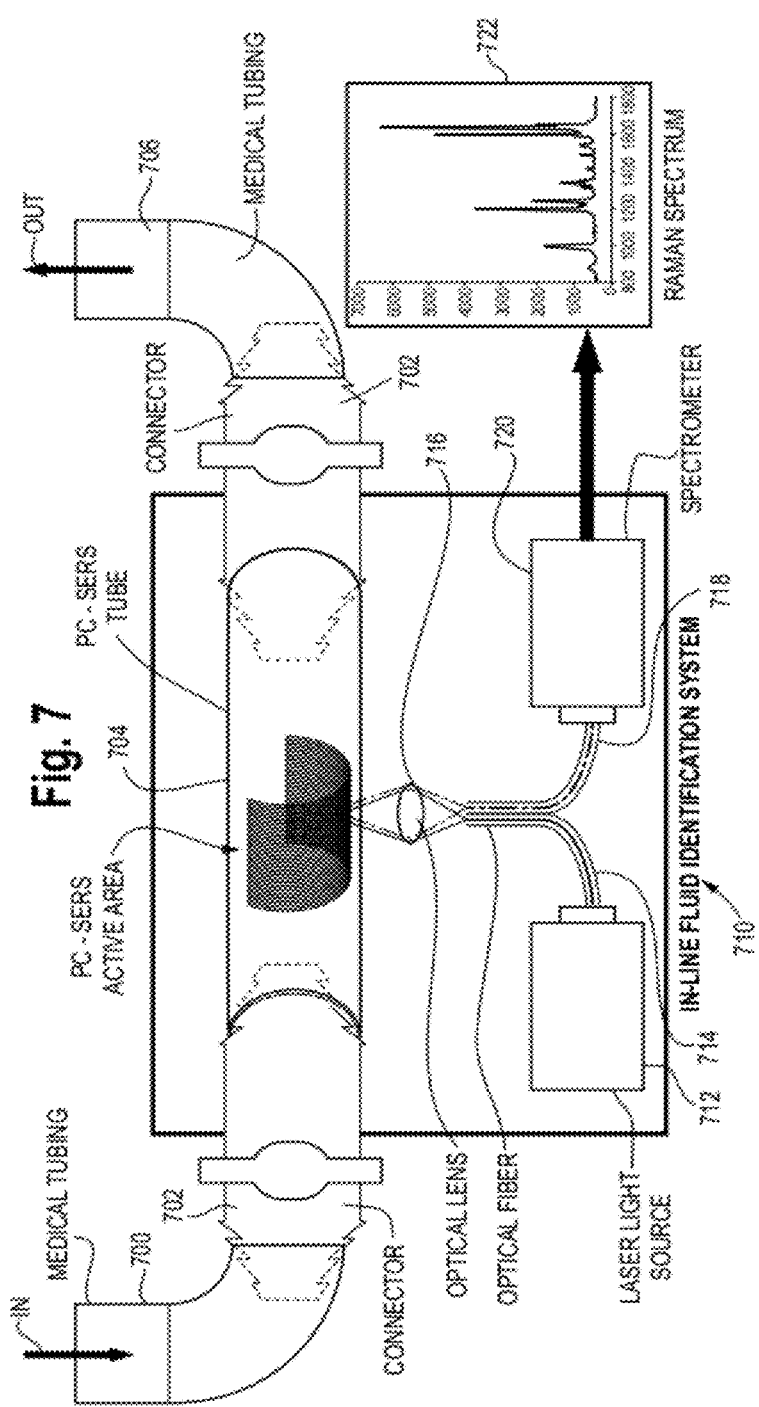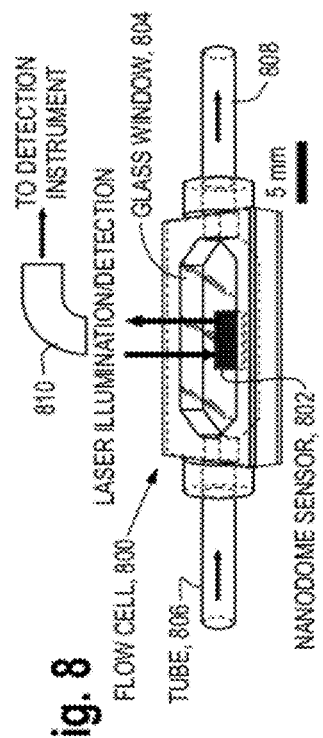

SURFACE ENHANCED RAMAN SPECTROSCOPY NANODOME BIOSENSORS AND METHODS OF MANUFACTURING THE SAME

CROSS-REFERENCE TO RELATED APPLICATIONS

This application claims priority benefits to U.S. provisional applications 61/575,391 filed Aug. 18, 2011 and 61/518,124 filed Apr. 29, 2011, the contents of both of which are fully incorporated by reference herein, including attached appendices. This application is also a continuation-in-part of application Ser. No. 12/586,516 filed Sep. 29, 2009, which claims priority to U.S. provisional application Ser. No. 61/195,133 filed Oct. 3, 2008. This application is also related to a patent application of Brian T. Cunningham et al. filed on the same date as this application, application Ser. No. 13/438,969, entitled "Photonic biosensors incorporated into tubing, methods of manufacture and instruments for analyzing the biosensors."

STATEMENT OF GOVERNMENT SUPPORT

This invention was made with government support under contract numbers CMMI0749028, DMI 0328162 and ECCS0924062 awarded by the National Science Foundation. The government has certain rights in the invention.

BACKGROUND

Biosensors, including optical biosensors, are generally known in the art and can take a variety of forms. U.S. Pat. Nos. 7,875,434 and 7,148,964 disclose photonic crystal sensors, including sensors which are incorporated or mounted to multi-well plates and similar devices. Other patent documents disclosing photonic crystal sensors include U.S. Pat. Nos. 7,118,710, 7,094,595, and 6,990,259; U.S. published patent applications 2007/0009968; 2002/0127565; 2003/0059855; 2007/0009380; and 2003/0027327.

Distributed Feedback Laser Biosensors (DFBLB) are also known in the art, see published patent application US 2009/0179637.

A third type of biosensor known in the art is referred to as a Surface Enhanced Raman Spectroscopy sensor (SERS).

It is known in the art that biosensors can be integrated with microfluidic flow channels fabricated on a substrate that is separate from the biosensor substrate, or integrated (i.e. co-fabricated) with the biosensor as disclosed in U.S. Pat. Nos. 7,531,786 and 7,737,392 to B. T. Cunningham and C. J. Choi, and in the publication of C. J. Choi and B. T. Cunningham, "Single-step fabrication of photonic crystal biosensors with polymer microfluidic channels by a replica molding process," *Lab-On-A-Chip*, Vol. 6, p. 1373-1380, 2006. Such devices generally have a flow cross sectional area that is too small for carrying large volumes of fluid, and thus are not suitable for in-line use for applications that require substantially large volume flow rates.

Additional prior art of interest includes U.S. Pat. Nos. 7,289,690, 7,314,751, and US patent application publication 2009/0051913.

SUMMARY

In a first aspect, a Surface Enhanced Raman Spectroscopy (SERS) biosensor is disclosed comprising an array of closely-spaced metal nanodomes fabricated on a flexible plastic film.

In one embodiment, the SERS nanodome sensor includes a substrate, such flexible clear plastic, e.g., PET, a periodic surface grating structure applied to the substrate, a material such as $SiO_2$ deposited onto the periodic surface grating structure to thereby provide an array of dome-like structures projecting above the substrate, and a metallic coating (e.g., silver or gold) deposited on the dome-like structures. The nanodomes can be manufactured as a two-dimensional array of domes on a flexible plastic substrate in a preferred manufacturing method. The dome-like structures preferably have a spacing between each other in the range of about 10-30 nm, and more preferably between about 10 and about 20 nm.

The biosensors of this disclosure can be incorporated into a variety of sample testing devices including a tube (e.g., plastic or glass), the biosensor placed in fluid communication with the contents of the tube; a liquid-containing vessel, the biosensor placed in fluid communication with the contents of the vessel; c) a glass slide; d) a test tube; and e) a flow cell.

In another aspect, a method of manufacturing a Surface Enhanced Raman Spectroscopy (SERS) nanodome sensor is disclosed. The method includes the steps of providing a flexible plastic substrate; forming a two-dimensional periodic grating structure on the substrate using a replica molding process; depositing a material on the two-dimensional periodic grating structure to thereby form a two-dimensional periodic array of nanodomes on the substrate; and depositing a thin film metal layer on the two-dimensional periodic array of nanodomes.

In still another aspect, a biosensor detection arrangement is disclosed comprising: a) SERS nanodome sensor, b) a detection instrument including a laser illumination source and a spectrometer; and c) a holding fixture for holding the SERS nanodome sensor relative to the detection instrument. For example, in this detection arrangement the SERS nanodome sensor is incorporated into a section of tubing such that the SERS nanodome sensor is placed in fluid communication with the contents of the tubing, and wherein the holding fixture provides for relative movement between components of the detection system and the section of tubing.

Another aspect of this disclosure relates to a biosensor comprising the combination of a Surface Enhanced Raman Spectroscopy (SERS) nanodome biosensor comprising an array of closely-spaced metal nanodomes fabricated on a flexible plastic film and a second photonic biosensor different from the SERS nanodome sensor, and a tube or flow cell incorporating the combination of the (SERS) nanodome biosensor and the second photonic biosensor. In one embodiment, the second photonic sensor is in the form of a distributed feedback laser biosensor, and wherein the SERS nanodome biosensor and the distributed feedback laser biosensor are formed on a flexible plastic film and arranged in a spaced apart arrangement, wherein a first region of the flexible plastic film contains the SERS nanodome biosensor and a second region of the flexible plastic film contains the distributed feedback laser biosensor.

In one aspect, this disclosure describes chemical and biological photonic sensors that are fabricated on flexible plastic film and placed in fluid communication with the contents of plastic or glass tubing, such as incorporated into the inner surfaces of the tubing or wrapped around the tubing with a window in the tubing material in registry with the photonic sensor. Exemplary descriptions are provided of different types of optical biosensors that can be fabricated inexpensively from plastic material on a flexible flat substrate, and then rolled to produce a section of tubing. While rolling the sensor into a curled section is the preferred embodiment, several additional embodiments are also described, including supporting the sensor within a section of tubing. The photonic biosensor is measured by illuminating the sensor though the outside surface of the tubing, and by subsequently capturing light that is reflected, scattered, or emitted from the sensor on the inner surface of the tubing. The tubing format is enabled by biosensor geometries that are able to function while in a curved configuration. The biosensor tubing may be connected in series with conventional tubing.

Another aspect of this disclosure relates to methods of manufacturing a photonic biosensor. In one method, a flexible plastic film if obtained having a photonic sensor region formed on a surface thereof. The method includes the step of forming the flexible plastic film into a tube having an interior surface and an exterior surface with the photonic sensor region on the interior surface of the tube. The method may also include the steps of connecting the tube to a section of tubing (e.g., medical tubing, catheters, infusion pump lines, blood tubing set, etc.) with the aid of tubing connectors. In one possible embodiment the photonic sensor region can take the form of a spaced array of individual photonic sensor areas.

An alternative method of manufacturing a photonic biosensor includes the steps of forming a window in a tube and wrapping a flexible plastic film having a photonic sensor region formed on a surface thereof over the tube with the photonic sensor region placed within the window in communication with the interior of the tube.

Another method of manufacturing a photonic biosensor includes the steps of forming a flexible plastic film having a photonic sensor formed on a surface thereof into the form of a tube to produce a segment of photonic sensor tubing, and inserting the photonic sensor tubing into a second piece of tubing and retaining the photonic sensor tubing in place within the second piece of tubing, e.g., with an adhesive or other bonding technique.

In still another method of manufacturing a photonic biosensor, the method includes the steps of placing a flexible plastic film having a photonic sensor formed on a surface thereof onto a support, placing the support within a section of tubing and retaining the support within the section of tubing.

Another aspect of the disclosure relates to the placement of the sensors of this disclosure on the inner surface of liquid-containing vessels generally, including for example test tubes, flasks, beakers, centrifuge tubes, flow cells, microwell plates receiving fluid samples, and the like. The methods for placement of the biosensors can be extended to installation on the surface of the liquid-containing vessels. The principle of operation of the detection instrumentation in these embodiments is the same for the tubing embodiments.

In the embodiments of tubing and in liquid-containing vessels, the sensor per se could be curved in order to fit flush with the wall of the tubing or liquid-containing vessel. Alternatively, the sensor could have a flat or essentially flat configuration and be placed within the tubing or the liquid-containing vessel in any suitable manner. Examples are shown below in conjunction with the drawing figures, and these examples can be carried out in other types of liquid-containing vessels. For example, in a flow-cell, the wall of the flow cell may have a flat portion and the sensor is adhered to or otherwise incorporated into the flat portion of the flow cell.

The applications for the sensors of this disclosure are many, including chemical testing and biological testing applications. One of the benefits of the present disclosure is that it describes sensor configurations, detection instrument configurations, and fabrication methods that are suitable for incorporating chemical and biological photonic sensors into the inside surfaces of plastic (or glass) tubing and which are capable of general purpose use. We envision tubing with inside diameters ranging from 1 mm to 1000 mm for applications that require volumes of fluid that are greater than those supported by microfluidic chips. These applications include, among others, tubing used in hospital care (e.g., urinary catheters, intravenous fluid delivery tubing, tubing used in dialysis, e.g. heparin lines or blood tubing sets), food manufacturing, pharmaceutical manufacturing, water quality monitoring, and environmental monitoring. For these applications, it is generally not desirable to add anything (such as fluorescent dyes or nanoparticles) to the liquid being tested that would contaminate the product or be introduced to a patient's body. It is also desirable for a sensor technology to operate in a continuous manner that does not require periodic sampling of the fluid being monitored, so as to reduce the risk of contamination of the fluid. The sensors of the present disclosure enable this.

Thus, the photonic sensors of this disclosure are typically "label-free" and enable a simple interface between the photonic sensor itself (which is in contact with the fluid being monitored) and the detection instrument that reads signals from the sensor which is outside the tubing. Optical biosensors provide this capability because the sensor is illuminated from an external source, and the detection instrument measures characteristics of the light that is reflected, emitted, or scattered from the sensor. For exemplary optical biosensors, no electrical contact or other physical connection is required between the sensor and the detection instrument.

Three photonic biosensors that meet these objectives and which can be used in the tubing-based biosensors of this disclosure are 1) Photonic crystal biosensors, 2) Distributed Feedback Laser Biosensors (DFBLB), and 3) SERS sensors including photonic crystal-enhanced Surface Enhanced Raman (PC-SERS) sensors.

The analytes that can be detected with these three sensor technologies include bacteria, viruses, proteins, chemical contaminants, metabolites, and drugs.

An array of sensors may be incorporated into a single section of tubing, with each sensor in the array prepared with an immobilized capture molecule for detection of a specific analyte from the fluid flow. Therefore, several analytes may be monitored simultaneously.

Multiple sensor types may be integrated together, so that a single section of biosensor tubing may perform biological analysis (such as monitoring for bacterial pathogens) and chemical analysis (monitoring the concentration of a particular chemical in a urinary catheter).

A still further aspect of this disclosure is that novel products, processes and instrumentation are provided. An example of a new product includes biosensor tubing as described herein. The disclosure describes several possible processes for making biosensor tubing. The tubing biosensor represents a new format for several optical biosensor technologies that have previously been demonstrated in "flat" non-tubing formats. Novel instrument arrangements are also provided for obtaining information from the sensor.

These and still other aspects of the present disclosure will be more completely explained in the following detailed description. All questions concerning the scope of the invention are to be answered by reference to the appended claims.

BRIEF DESCRIPTION OF THE DRAWINGS

FIG. 2E is a plot of single mode output of the sensor in aqueous medium demonstrating dynamic tuning of the laser wavelength for deposition of a series of positive and negative charged alternating polymer monolayers. FIG. 2F is a demonstration of laser wavelength shift measurements for a small array of 6 DFB laser biosensors for detection of IgG antibody molecules for a range of concentrations, demonstrating the ability to monitor the kinetic characteristics of protein binding.

FIG. 3F is a plot of the relationship between SERS laser coupling angle and measured SERS intensity, showing the magnitude of the resonance enhancement, and the measured signal relationship with the calculated electromagnetic field intensity on the PC surface.

FIG. 4 is schematic diagram of the process used to produce a section of plastic biosensor tubing from a rectangular coupon. The tubing section containing the sensor is wrapped around existing tubing, with the existing tubing having a hole such that the sensor is in fluid contact with the contents of the tube. The sensor tubing segment is connected in series with ordinary plastic tubing using standard connectors.

FIG. 7 is an illustration of a section of tubing incorporating a PC-SERS sensor and the associated detection instrumentation consisting of laser light source, spectrometer, optical fibers and an objective lens.

FIG. 8 is an illustration of a flow cell having a PC-SERS nanodome sensor placed within the flow cell and showing laser illumination of the sensor for detection.

FIG. 11(a) shows an Ag coated nanodome array substrate with measured dome separation distance of 17 nm. FIG. 11(b) is a close-up view of the nanodome array in FIG. 11(a). FIG. 11(c) is a perspective view of the nanodome array substrate in FIGS. 11(a) and (b). FIG. 11(d) illustrates an Ag coated nanodome array substrate with measured dome separation distance of 84 nm. FIG. 11(e) illustrates an Ag coated nanodome array substrate with domes touching each other. FIG. 11(f) illustrates UV cured polymer replica molded on a flexible plastic substrate before $SiO_2$ and Ag deposition to form the nanodomes.

DETAILED DESCRIPTION

1. Introduction and Overview

Figure 1:
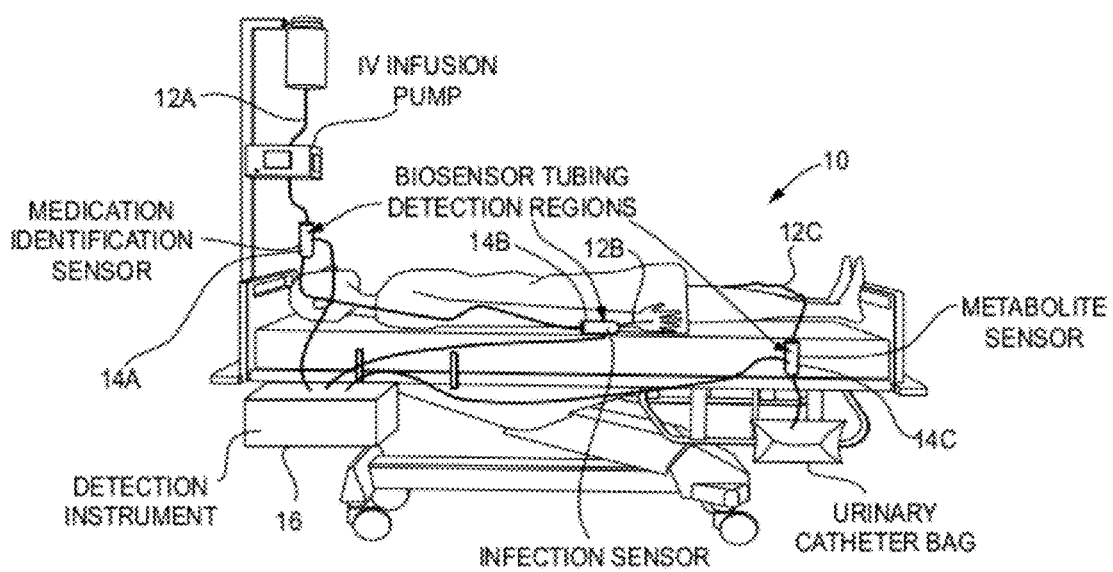
FIG. 1 is a schematic illustration of a patient having medical tubing incorporating photonic sensors in fluid communication with the contents of the tubing, and an associated detection instrument for reading the sensors. The tubing in FIG. 1 is an IV line, a catheter and a blood line. These are just some examples of tubing with photonic sensors and are offered by way of example and not limitation.

In 2010, over 350,000 Americans used dialysis to supplement their kidney function and this number is expected to grow substantially in the future, as more than 26 million Americans have Chronic Kidney Disease as a result of diabetes and high blood pressure or other causes. At the same time, a wide range of drugs and fluids are administered to millions of patients each year using pumped intravenous (IV) delivery, often in combinations used to treat multiple conditions at once. Within the intensive care unit of hospitals, bedridden patients are routinely fitted with urinary catheters that allow drainage of their bladders, and laboratory-based tests are performed upon urine samples to periodically monitor the concentrations of excreted metabolites.

A characteristic that is shared by all three of these common medical practices is the use of disposable sterile plastic tubing to deliver fluids to or from the patient. As the US health care industry seeks to more effectively provide medical treatment, the concept of "intelligent" systems that are capable of gathering sensor readings from bodily fluids that provide accurate and timely information on the status of a patient to medical staff, or that can reduce the incidence of medication delivery errors has gathered momentum. However, an important bottleneck to the translation of such systems to clinical practice has been the prohibitive cost/complexity of sensors, and their lack of compatibility with the fluid handling methods commonly used in hospitals.

Detection and identification of the chemical or biological contents of fluid within a flow stream is a critical component of systems used for medical diagnosis and medication delivery. For example, in-line monitoring of the components of bodily fluids, such as blood and urine, have become a priority in clinical care. In some situations, such as dialysis, a bodily fluid may be analyzed before and after an ex-vivo filtration process in which the fluid will be returned to the patient's body. Likewise, the ability to continuously monitor the contents of an intravenous (IV) line being used to deliver medication to a patient for validation of the desired drug and the presence of contaminants (both chemical and bacterial) would offer a means for minimizing the occurrence of medication errors while at the same time detecting the onset of infections before they become life-threatening. In a similar fashion, the ability to continuously monitor the chemical contents of urine flowing through a catheter would enable noninvasive monitoring of well-established chemical biomarkers for renal function and metabolism.

In these clinical scenarios, particularly those that involve the monitoring of fluid that is introduced to the patient's body, it is not permissible to add foreign material to the fluid (such as fluorescent dyes or nanoparticles) that may harm the patient. It is also not permissible withdraw small samples from the fluid using methods that may compromise sterility. Therefore, label-free methods that enable detection of analytes in the flow stream using their intrinsic physical properties, such as dielectric permittivity or molecular vibrational modes, are most desirable. Further, label-free detection that would allow a sterile sensor to be placed within the flow stream, but that can be monitored from outside the flow stream with a noncontact probing/readout method is required. Clinical diagnostic tests are required for monitoring of a wide range of chemical and biological analytes, that may include drug compounds, metabolites, proteins, and bacteria. Because detection of some analytes requires specific chemical identification, while other analytes may be specifically detected most effectively using affinity capture assays, the ability to integrate multiple detection modalities into a single detection system would offer a highly complementary set of information regarding a patient's status. While detection of clinically relevant concentrations of chemical analytes can be performed in the mg/ml range, detection of certain protein biomarkers, and bacterial particles demand a high degree of sensitivity and resolution that necessitates the use of multiplexed sensors for incorporation of replicates and negative controls that can reduce the incidence of false positive and false negative results. However, none of these capabilities would make a transition to clinical care unless they can be inexpensively produced and seamlessly integrated with the existing fluid-handling infrastructure used for intravenous medication delivery, dialysis, and catheterization. This invention meets this need.

In this disclosure, we describe a photonics-based sensor system that is incorporated into tubing such that the photonic sensor surface is in fluid contact with the contents of the tubing. The tubing can for example be generic, disposable clear plastic tubing. In one possible configuration, the sensors of this disclosure can be fabricated upon a flexible plastic surface and rolled into a cylinder, so that sensors form the inner surface of disposable plastic or glass tubing. Photonics-based label-free sensors are described which can be co-fabricated using a nanoreplica molding process, in mass production methods, at low cost. The sensors can also be formed on a thin flexible plastic substrate as a "coupon" and then wrapped around existing tubing. The existing tubing has a window or hole formed in it and the sensor area of the "coupon" is placed over the window such that fluid flowing through the tubing is in contact with the sensor area. The coupon can take the form of an array of sensor locations, each sensor location provided with specific capture molecules for detection of a separate analyte of interest in the fluid.

One of the photonics-based sensors suitable for use with tubing is a label-free affinity biosensor based upon a plastic Distributed Feedback (DFB) laser, recently demonstrated by the inventors' research group. See US patent application publication US 2009/0179637. The techniques of this sensor design can be used for, among other things, multiplexed high sensitivity detection of protein biomarkers and bacteria. The DFB laser biosensor surface is prepared with specific capture molecules (such as antibodies) that selectively bind to their analyte from the flow stream. Adsorption of the analyte on the DFB laser surface results in a positive shift in the emission wavelength of the laser. Optical pump excitation and emission wavelength detection of the DFB laser biosensor is performed by an instrument that will clamp around the tubing and serially probe multiple locations.

A secondly photonics biosensor suitable for incorporation into tubing is Photonic-Crystal-Enhanced Surface Enhanced Raman Spectroscopy (PC-SERS), with which specific chemical identification of analytes within the flow stream can be performed. PC-SERS, as recently demonstrated by the applicant's laboratory (see US patent application publication US 2010/0085566), increases the detection sensitivity of ordinary metal particle-based SERS over an order of magnitude through coupling of a metal nanoparticle surface to the resonant modes of a Photonic Crystal (PC) surface. PC-SERS entails excitation of vibrational modes of chemical molecules in contact with a metal surface with a laser with a specific wavelength selected to match the resonant mode of the PC, and detection of the scattered spectrum with a spectrometer. The presence and concentration of chemical compounds with known SERS scattering spectra can be monitored by measuring the intensity of the SERS spectra at specific wavenumbers. Like the DFB laser biosensor, the PC-SERS structure may be fabricated in flexible plastic material using a nanoreplica molding process, and the PC-SERS detection instrument utilizes an excitation laser and spectrometer than can be fashioned into a form that allows clamping around the exterior of the tubing.

In addition, photonic crystal label-free biosensors, previously developed by one of the inventors (Cunningham) and disclosed in the patent literature cited in the Background section of this document, may also be integrated into tubing format.

2. Photonic Sensors in Tubing for in-Line Continuous Monitoring for Clinical Diagnostics: Metabolites, Drug Delivery, and Pathogens While this disclosure will is focused on applications for an in-line label-free detection system in certain clinical diagnostics based upon photonic sensors incorporated into tubing such as PC sensors, DFB laser biosensors and PC-SERS sensors, the technology is broadly applicable to a wide range of clinical diagnostic problems, industrial process monitoring, food manufacturing, water quality monitoring, and environmental monitoring, in which the contents of a continuous flow stream must be monitored. As exemplary applications, this disclosure will include a focus upon three different types of analytes: 1). Metabolites, 2). Drug Compounds, and 3). Bacterial Pathogens. For each class of analyte, we have selected 1-2 representative analytes that can effectively demonstrate the capabilities of the sensors of this disclosure.

FIG. 1 is an illustration of an example of how the sensors of this disclosure can be used and incorporated into tubing. In FIG. 1, a patient 10 receives intravenous medication via IV tubing 12A, which has incorporated therein a photonics sensor 14A used for sensing the presence of drug compounds in the IV medication. Blood from the patient is collected via a tube 12B having a sensor 14B therein for detection of bacterial pathogens. A catheter 12C includes a photonics sensor 14C for detection of the presence of metabolites (urea, creatinine) in the patient's urine. A detection instrument 16 with associated optical fiber cabling is used for directing light (e.g. laser light) onto the tubing at the location of the sensors 14A, 14B and 14C. Optical fibers collect reflected radiation and direct the radiation back to the detection instrument 16 for analysis as explained in detail below, e.g., to determine if the correct drug compound is present in the IV fluid, to determine the presence of a bacterial pathogen in the patient's blood, and to monitor metabolite concentrations in the patient's urine.

A. Metabolites

The concentrations of creatinine and urea in blood and urine are widely used for characterizing kidney function. Creatinine is a protein produced by muscles with a concentration that is relatively stable in healthy people. Due to the large fluctuations in the amount of water dilution from sample to sample in urine analysis, creatinine is used as an internal reference concentration to normalize water variations. Creatinine concentration also provides information about muscular dystrophy, hyperthyroidism and poliomyelitis, while integrated creatinine measurements over the course of a day reflect the efficiency of the kidneys' filtration function. Urea is the main and final product of protein metabolism, thus its concentration in urine is used as an indicator of the nutritional status of a patient, while its concentration in blood is useful for diagnosis of renal dysfunction. During kidney dialysis, creatinine and urea are recognized as markers for a wide spectrum of low and intermediate-molecular mass toxic solutes accumulated in patients with diminished renal function.

A number of laboratory-based measurement methods are available for creatinine and urea. For example, adding particular enzymes to a test sample converts the analyte into ionic products that enable conductometric or potentiometric techniques to indirectly measure their concentration. However, these methods require periodic sampling of blood or urine, and are not appropriate for in-line use. Spectroscopic methods including fluorescence, absorption and scattering have also been demonstrated for measurement of creatinine and urea. The fluorescence method requires addition of fluorescent reactants and thus is not suitable for in-line use. In infrared absorption spectroscopy, a selected band of near-infrared light is transmitted through the sample, and the analyte concentration is obtained by analysis of the resulting spectral information. This method is nondestructive and reagentless, thereby permitting in-line identification. However, due to the relatively high detection limit and heterogeneous characteristic of bodily fluid, it is hard to detect creatinine with a sufficient accuracy. The normal levels of creatinine and urea in bodily fluid are 71-276 μM and 2.5-6.7 mM, respectively, requiring methods with higher sensitivity than absorption spectroscopy. Raman spectroscopy has been successfully demonstrated as a successful means for urea and creatinine detection in bodily fluid using both human urine and an artificial urine control that contains about the same concentrations of the urea, creatinine and uric acid as in healthy human urine. The primary Raman band near 1,000 $cm^{-1}$ corresponds to the symmetrical C—N stretch and may be used for urea analysis directly. Raman spectra of aqueous creatinine solutions and comparison to SERS spectra the same concentrations shows multiple distinct peaks in the 700-900 $cm^{-1}$ range, and that SERS can significantly increase the Raman signal for measurement of creatinine in bodily fluid at clinically relevant concentrations.

PC-SERS photonic sensors as described herein are suitable for incorporation into tubing to detect metabolites, as will be explained in further examples below.

B. Drug Compounds

Rapid identification and verification of the chemical contents of a fluid being administered to a patient provides an opportunity to avoid medical errors due to mislabeled product, or incorrectly selected fluid bags. An independent measurement of the contents of an IV line would provide an additional layer of error-checking to ensure that medications being delivered in combinations have no unfavorable interactions, and that the correct medications are paired with the correct delivery rate. A system for fluid identification must be able to perform as a "closed system" that does not require extraction of a fluid sample from the line, maintains sterility of the delivered fluid, and is able to perform monitoring continuously. These requirements also dictate that no additional analytes may be added to the fluid to facilitate detection, so chemicals must be identified using some intrinsic property that still allows one chemical to be distinguished from another.

The drugs that are most commonly administered by IV infusion pumps are also the same products that are associated with patient harm or death in the hospital, because they are mistakenly administered to the wrong patient, at an incorrect dosage, or in combination with another drug with an adverse interaction. In rank order, the drugs with the five highest rates of mortality due to delivery errors are: 1.) Insulin, 2). Morphine, 3). Heparin, 4). Warfarin, and 5). Hydromorphone. These drugs are followed by additional common pain medications and anti-bacterial medications (Vancomycin, Enoxaparin, Furosemide, Dopamine). Due to their commercial availability and lack of restrictions for usage in the laboratory, we will focus on detection of Insulin and Heparin using the PC-SERS sensor.

Because the drugs are present within their carrier fluid at concentrations greater than 1 mg/ml, detection of these materials does not pose a particularly great sensitivity challenge. However, in this situation, it is important for the drug within the fluid line to be identified rapidly, so a long "integration time" to obtain a conclusive measurement is undesirable, and the ability to perform SERS measurements with an inexpensive, low power laser is required. Raman and SERS spectra for drugs including insulin and heparin have been well characterized, and their unique scattering peaks identified.

Accordingly, PC-SERS sensors and the Raman nanodome sensors described later in this document are suitable for incorporation into tubing for the detection of drug compounds.

C. Bacterial Pathogens

Detection of bacterial pathogens within the blood stream, dialysis fluid, and catheters represents an important opportunity to develop smart medical systems that are capable of quickly diagnosing the onset of infection before symptoms become severe. However, bacterial detection and identification methods based upon culture, polymerase chain reaction (PCR), or enzyme-linked immunosorbent assays (ELISA) require long and/or complex laboratory procedures that must be performed upon a test sample taken from the patient. Performing such procedures in the context of a sterile "closed system" that may involve return of fluids to the patient's body is not possible due to the potential for introducing a new infection. Therefore, the ability to perform detection assays upon intact pathogens is required.

For bloodstream infections introduced through IV lines, the bacteria coagulate negative Staphylococci represents ~37% of all cases, followed by *Pseudomonas aeruginosa* (14%), *Candida albicans* (8%), Enterococci (8%), and *Staphylococcus aureus* (MRSA) (8%). Due to the prevalence of Staphylococci infections, our goal will be to utilize the DFB laser biosensor with immobilized capture molecules that selectively bind with outer surface proteins on the Staphylococci bacteria for rapid, high sensitivity detection of intact bacteria. This approach has been demonstrated using other types of label-free biosensors such as quartz piezoelectric biosensors with immobilized lectin, and surface plasmon resonance (SPR) optical biosensors using immobilized phage. Although it is common to interface sensors such as these to microfluidic channels in the context of a low flow-volume chip, they have never been applied in the context of an in-line flow system.

Accordingly, DFB laser biosensors are suitable for incorporation into tubing for detection of bacterial pathogens, as will be explained in further examples below.

Example 1

Dfb Laser Biosensors Incorporated into Tubing, Flow Cells and Similar Devices

A wide variety of optical resonator structures have been used for label-free detection of chemical compounds, biomolecules, and cells. Several approaches have been commercially developed for applications in life science research, environmental monitoring, quality control testing, and diagnostic testing. Label-free resonant optical sensors generally detect shifts in resonant wavelength or coupling angle caused by the interaction between the target molecule and the evanescent portion of the resonant modes. The narrow spectral linewidth achieved by using high Q factor ($>10^5$) passive optical resonators enables sensor systems to resolve smaller wavelength shifts associated with the detection of analytes at low concentration, or detection of biomolecules with low molecular weight, such as drug compounds. While detection resolution can be substantially improved through the use of high Q factor passive resonators, the sensitivity and dynamic range of the system is generally decreased, although certain examples of passive resonators have achieved high Q factor and high sensitivity simultaneously. In addition, implementation of high Q factor optical resonators typically requires high precision alignment for evanescent light in/out coupling, providing potential limits to their practical application. Active resonator sensors, such as laser-based optical biosensors have been drawing special interest because they generate their own narrow linewidth stimulated emission, while retaining simple instrumentation and eliminating the requirement for high precision evanescent coupling to waveguides or tapered optical fibers. While our previous work demonstrated DFB laser biosensors fabricated upon a glass substrate using a sol-gel dielectric grating, practical biosensor applications demand an inexpensive fabrication method that can be performed over large surface areas. A large area, flexible, plastic-based sensor can be easily integrated with standard-format microplates, microarray slides, or flow tubing that interface easily with the fluid delivery infrastructure that is commonly used in life science research and medical applications. Our recent work has demonstrated a DFB laser biosensor that is fabricated with a plastic-based process on a flexible plastic substrate using a high surface-area nanoreplica molding process. See US patent application publication 2009/0179673. This advance is important to the eventual realization of single-use disposable biosensors made possible by mass-manufacturing of the sensor from continuous sheets of plastic film, in a similar fashion to the manufacturing methods used to produce photonic crystal biosensors, also developed by our group.

Figure 2A:
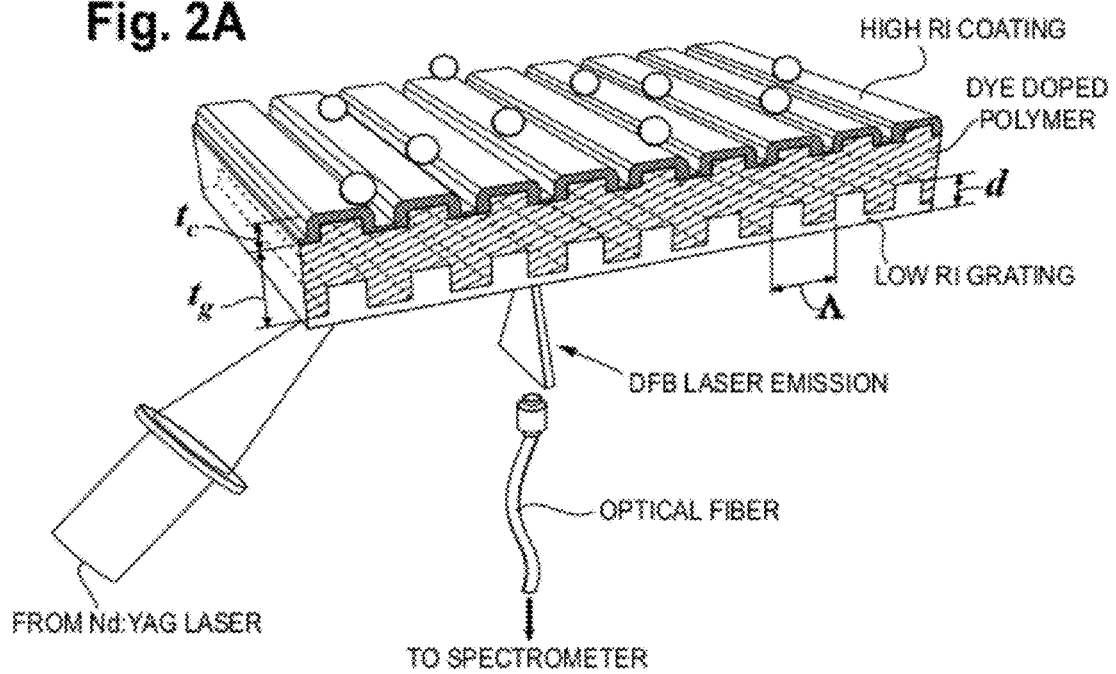
FIG. 2A is a schematic cross section diagram of a DFB laser biosensor suitable for use with the tubing of FIG. 1.

The DFB laser biosensor is based on a second order Bragg grating that supports a vertically emitting mode by first-order diffraction. A schematic cross-sectional diagram of the DFB laser structure is shown in FIG. 2a. The low refractive index polymer layer applied to the substrate functions as a cladding layer, upon which a thin film of high refractive index polymer provides vertical light confinement and feedback along the horizontal direction. Doped with laser dye, this high refractive index layer also contributes to the light amplification of the cavity oscillation mode. Altering the refractive index of the media exposed to the DFB laser surface or surface adsorption of biomolecules changes the effective refractive index associated with the resonant mode, and results in modulation of the stimulated emission wavelength. By controlling the guidance layer thickness, the DFB laser is designed to exhibit single mode radiation to facilitate determination of the laser wavelength shift.

Figure 2B:
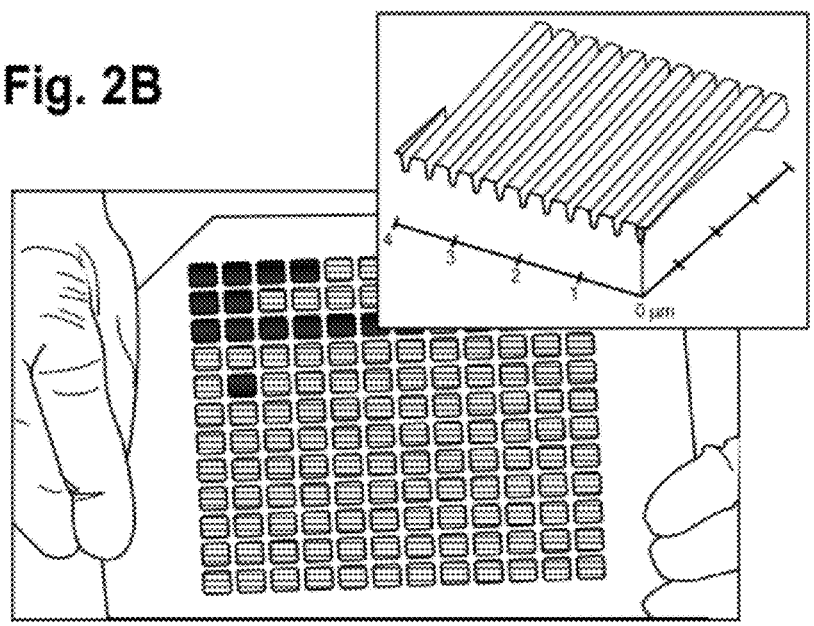
FIG. 2B is a photo of a ~3×5-inch replica molded array of DFB laser biosensors fabricated on a flexible plastic substrate and (inset) an AFM image of the surface topography of the grating structure.

The one-dimensional grating structure is produced with an ultraviolet (UV) curable polymer on a flexible polyethylene-terephthalate (PET) substrate film by a nanoreplica molding technique. A liquid UV curable polymer with n=1.39 was squeezed between the PET substrate and a silicon master wafer. The silicon stamp surface was produced by conventional electron-beam lithography and reactive ion etching. The replicated polymer grating was exposed to $O_2$ plasma for ~30 sec to render a hydrophilic surface. Atomic force microscopy verified that the replicated gratings have a period of $\Lambda$=400 nm and a depth of d=40 nm. The active medium was prepared by mixing a 5 mg/ml solution of Rhodamine 590 dye (Exciton) in $CH_2Cl_2$ with SU-8 (5.0 wt %; Microchem) to a volume percentage of 10%. This mixture was sonicated for improved homogenization and subsequently spin-coated onto the polymer grating surface at 5000 rpm for 30 seconds. The device was soft baked on a 95° C. hotplate for 1 min to remove the solvent, photopolymerized by exposing to UV radiation (365 nm lamp source) with exposure dose of 60 mJ $cm^{-2}$, and subsequently hard baked on a 95° C. hotplate for 2 min. The gain/waveguide layer has an overall thickness of ~300 nm and refractive index of n=1.58 as measured by ellipsometer (VASE, J. A. Woollam). A titanium dioxide ($TiO_2$) thin film was deposited on top of the DFB laser surface using an electron beam evaporator (Denton Vacuum) to improve biomolecular immobilization and sensor sensitivity. FIG. 2B shows a mass-production of the sensor of FIG. 2A with the grating shown highly magnified in the inset to FIG. 2B.

A replica-molded plastic-based vertically emitting DFB laser has been demonstrated for label-free chemical and biomolecular detection in which the emission wavelength is modulated by changes in bulk and surface-adsorbed material permittivity. When optically pumped with a ~10 ns pulse at $\lambda$=532 nm, the DFB laser exhibits stimulated emission in the $\lambda$=585-620 nm wavelength range with a linewidth as narrow as $\delta\lambda$=0.07 nm. While exposed to chemical solutions with different refractive index and adsorbed charged polymer monolayers, the laser sensor demonstrates single mode emission over a tuning range of ~14 nm and the ability to perform kinetic monitoring of surface adsorbed mass. A protein-protein interaction experiment was used to demonstrate the capability to characterize antibody-antigen affinity binding constants. These capabilities were recently demonstrated and are briefly summarized here.

Figure 2C:
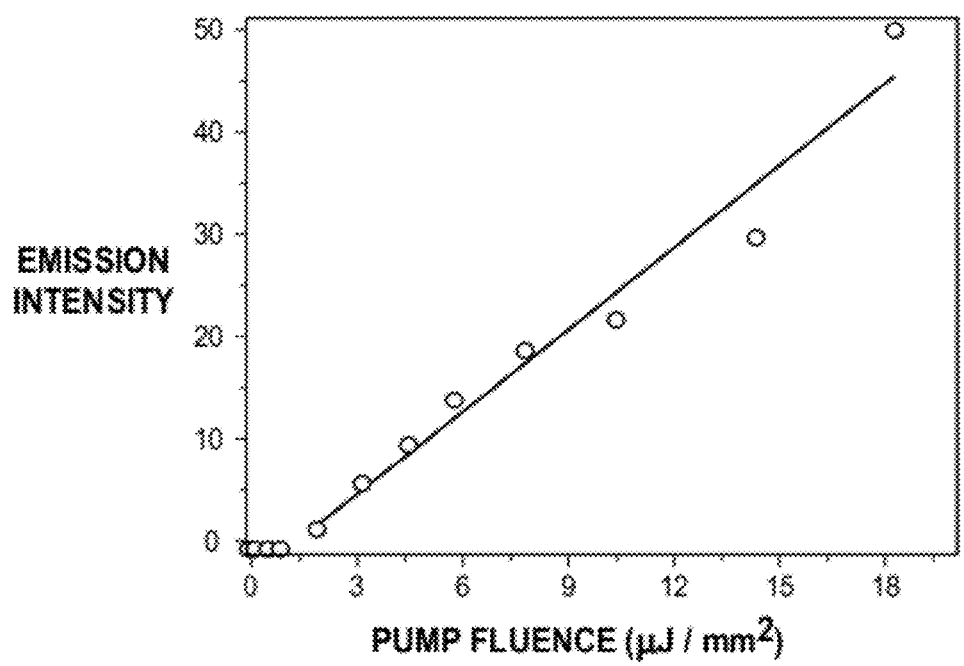
FIG. 2C is a plot of output emission intensity as a function of pump fluence for the sensor structure demonstrating the required fluence from a 532 nm pulsed excitation laser to excite DFB lasing.
Figure 2D:
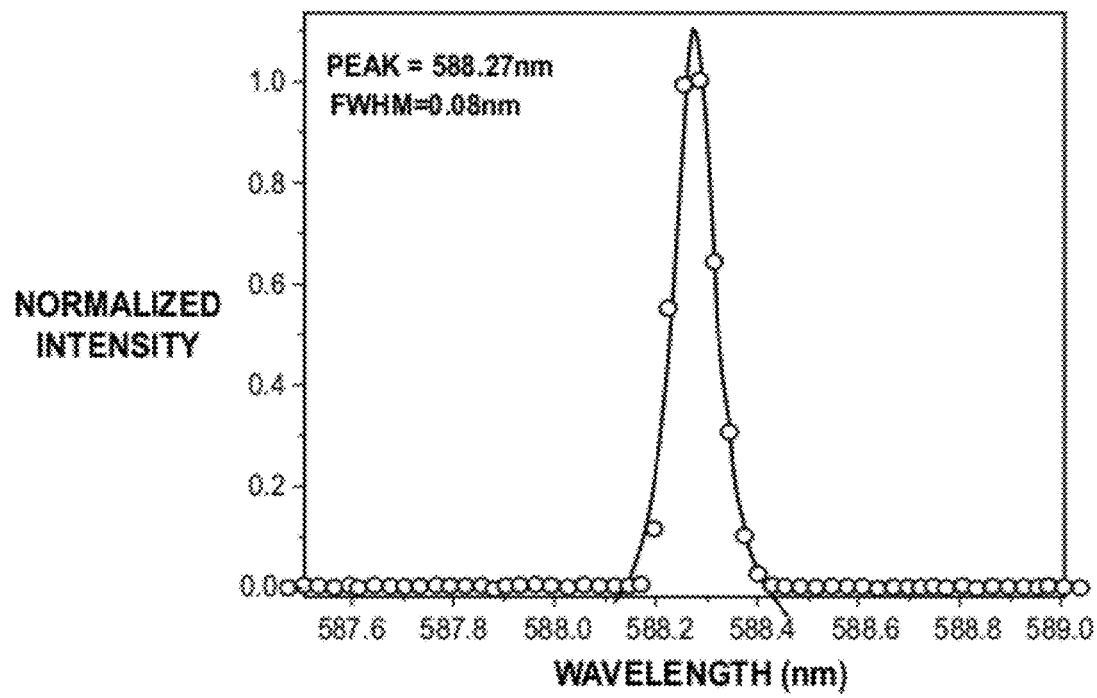
FIG. 2D is a plot of the single mode DFB lasing output spectrum for a fabricated structure measured in an air medium.

The DFB laser was optically excited by a frequency doubled, Q-switched Nd:YAG laser ($\lambda$=532 nm, 10 ns pulse width, single pulse mode) through a 600 μm diameter fiber and a focusing lens underneath the sensor surface (FIG. 2a). The emission from the DFB laser biosensor was coupled to a spectrometer (HR4000, Ocean Optics) through a detection fiber bundled with the excitation fiber. As illustrated by the inset of FIG. 2C, the dependence of the relative laser pulse energy on the pump fluence (measured by a pryoelectric detector) exhibits a clear threshold fluence of 1.09 $\mu J\text{-}mm^{-2}$. FIG. 2D shows the laser spectrum observed with the sensor surface exposed to air while pumped at 8.5 $\mu J\text{-}mm^{-2}$. The laser emission spectrum was fit to a Lorentzian profile, as shown in FIG. 2D to mathematically determine the center wavelength. Sensitivity to changes in the refractive index of media exposed to the sensor surface was measured by placing a droplet of water (n=1.333), acetone (n=1.359), isopropyl alcohol (n=1.377) and dimethyl sulfoxide (DMSO) (n=1.479) upon a single sensor in sequence. Single mode laser emission was measured for each solution, and a bulk refractive index sensitivity of $S_b=\Delta\lambda/\Delta n=99.58$ nm/RIU was measured, with linear behavior over the ~14 nm tuning range (data not shown).

In order to characterize the sensor sensitivity as a function of distance from the sensor surface, stacked alternating positively and negatively charged polyelectrolyte layers were deposited onto the sensor surface. The polyelectrolytes used in this work were anionic poly(sodium 4-styrenesulfonate) (PSS; $M_w$=60 kDa), cationic poly(allylamine hydrochloride) (PAH; $M_w$=70 kDa) and cationic poly(ethylenimine) (PEI; $M_w$=60 kDa) all dissolved in 0.9 M NaCl at a concentration of 5 mg/ml. The polyelectrolyte layer coating self-limits to a single monolayer with a refractive index of n=1.49 and thickness of ~5 nm. To build up the polymer stack, NaCl buffer was pipetted onto the sensor surface to establish a baseline and then replaced by PEI solution. After 10 min incubation, the PEI solution was removed and the sensor surface was washed with NaCl buffer. Six PSS-PAH alternating layers were deposited in sequence with a NaCl buffer rinse used after every PSS or PAH incubation. FIG. 2E shows the laser spectra measured at the end of each incubation step, and FIG. 2F illustrates the temporal progression of the laser wavelength shift for the PEI and six PSS-PAH depositions while the DFB laser wavelength was recorded at 30 s intervals. It should be noted that the initial PSS-PAH double layers (~10 nm) generate laser wavelength shifts of 2.2 nm with twice the magnitude of the following double layers. These results demonstrate that a single sensor may be queried many times over a substantial period of time without bleaching of the laser dye, thus enabling study of kinetic profiles of biomaterial adsorption. These results also illustrate that the sensor maintains single mode laser output over a wide wavelength dynamic range, and that the sensor wavelength shift response is not saturated after the deposition of a total thickness of ~60 nm material on its surface.

To demonstrate the ability of the sensor to detect biomolecules and to characterize the affinity binding constant of a protein-protein interaction with a simple procedure, Protein A was adsorbed to the surface using noncovalent hydrophobic attachment, and subsequently exposed to a human antibody under a range of concentrations. Protein A (Sigma-Aldrich; $M_w$=40 kDa) was dissolved in 0.01 M phosphate buffered saline (PBS; pH=7.4) solution to a concentration of 0.5 mg/ml, pipetted onto sensor surface, and allowed to incubate for 20 min at room temperature. Human IgG (Sigma-Aldrich, $M_w$=146 kDa) was dissolved in 0.01 M PBS solution to seven different concentrations (34 μM, 3.4 μM, 0.86 μM, 0.34 μM, 34 nM, 3.4 nM, and 0.68 nM). Seven different spots on the sensor slide were then rinsed and soaked in PBS buffer to establish an initial baseline emission wavelength. After 3-4 min, the PBS solution was replaced by a human IgG solution and stabilized for 10 min. Then the sensor surface was rinsed with PBS solution to remove any unbound IgG. The detection kinetics for human IgG at different concentrations are shown in FIG. 2F with spectra measured every 15 s. The high concentration (>10 μM) human IgG detection approaches saturation due to the limited number of Protein A binding sites on the sensor surface. The lowest concentration of human IgG (3.4 nM) resulted in an easily measured laser wavelength shift of $\Delta\lambda \sim 0.05$ nm.

The DFB laser biosensor shown in FIG. 2 can be incorporated into simple clear plastic or glass disposable tubing, flow cells, test tubes, and other similar devices, such as shown in FIGS. 1, 4, 5, 6, 7, 8, 9 and described later in this document.

Example 2

Photonic crystal ("PC") enhanced SERS sensors incorporated into tubing flow cells and similar devices.

Since the experimental demonstrations of Surface Enhanced Raman Spectroscopy (SERS) (Fleischman et al., *Chem. Phys. Letters* vol. 26, p. 163 (1974)) it has been shown that many molecules display Raman cross-sections that are several orders of magnitude greater when adsorbed upon roughened conducting surfaces than the corresponding quantity in solution or on an ordinary smooth surface. Due to the surface enhancement, small sample volumes can be detected with concentration resolution in the picomole to femtomole range, making the SERS technique potentially attractive for detecting trace quantities of explosives, drugs-of-abuse, environmental contaminants, and biological pathogens. The mechanisms by which the SERS effect occurs are currently debated, and two main enhancement routes have been proposed, namely the electromagnetic (EM) effect and the chemical enhancement (CE) effect. The present disclosure is concerned only with the EM effect, in which the local EM field at the surface of a metal is significantly changed from that of the incident field, and becomes more pronounced when fine metal particles or rough surfaces generate local surface plasmon resonances. The EM effect results in enhanced excitation of Raman vibrational modes due to highly localized EM fields that can be substantially higher than the electric-field of the incident laser illumination. An extensive literature exists on the effects of metal surfaces for SERS, and on the use of a variety of metal surface configurations (planar, corrugated, colloidal) or metallic particle types (spheres, shells, boxes, and triangles to name just a few) that involve plasmonic resonances to enhance EM excitation. Although enormous enhancement factors have been achieved using metal structures, further enhancement of Raman signals is still desirable to reduce laser power and accumulation time for detection of trace quantities of analytes. A previous publication described the use of a dielectric-based ring resonator for obtaining additional enhancement of the EM field around metal nanostructures for SERS (White et al., *Opt. Express* vol. 51 (1992)). Here, we demonstrate that the near-fields of a Photonic Crystal (PC) slab optical resonator can also efficiently couple light from a laser to metal nanostructures on a PC surface.

The surface PC used in this work is a subwavelength periodic arrangement of dielectric materials that can support guided-mode resonances at designated wavelengths, where the device reflects ~100% of incident light at the resonant wavelength while all other wavelengths are transmitted. See generally US patent application publication US 2010/0085566. Under resonant conditions, excited leaky modes are localized in space during their finite lifetimes, which enhance the near electric-field intensity of the PC structure, and thus enhance the SERS signal from adsorbed molecules on metal nanostructures in close proximity to the PC. The PC-coupled SERS substrate (PC-SERS substrate) can be an effective means for increasing SERS enhancement factor. The PC-SERS surface is inexpensively fabricated using a plastic-based large-area replica molding process for the PC and a uniform and simple physical deposition technique for the SERS metal nanoparticles. High additional enhancement of EM fields can be obtained using high Q-factor PC resonators while Raman scattered light can be efficiently directed toward a detector using the PC-enhanced extraction method demonstrated in previous publications with fluorescence extraction. See US patent application publication US 2008/0278722. We used the Glancing Angle Deposition (GLAD) technique to create a high density coating of electrically isolated Ag nanoparticles that are supported vertically from the PC surface upon 50 nm-tall $SiO_2$ dielectric posts. The GLAD technique has been demonstrated to be a simple method for fabrication of metal structures with high SERS enhancement factor because the randomly distributed and sized Ag nanostructure have numerous interconnections and strong EM field within the gaps between the nanoparticles. To examine optical coupling between resonant near fields from the PC and metal nanoparticles in close proximity to the PC surface, we performed computer simulations of the electric field distribution around a single exemplary metal particle.

Figure 3A:
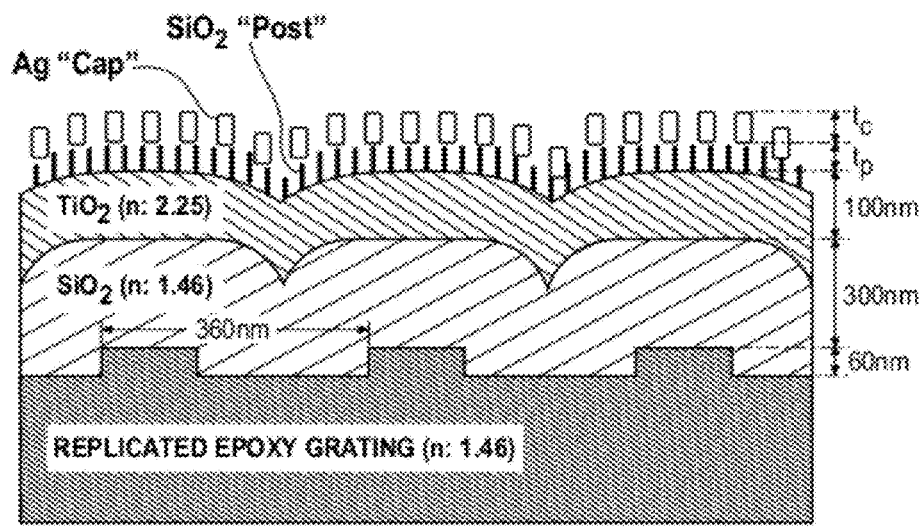
FIG. 3A is a cross-section diagram of a PC-SERS structure, comprised of a replica molded linear grating surface structure on a flexible plastic substrate that is subsequently coated with dielectric coatings of $SiO_2$ and $TiO_2$ to produce a guided mode resonant filter with a resonance at the laser wavelength used for SERS.

FIG. 3a shows a cross sectional schematic of the PC-SERS substrate, comprised of a 1-dimensional PC slab and a $SiO_2$—Ag "post-cap" nanostructure coating. To fabricate the PC, a polymer grating (period=360 nm, depth=60 nm) was fabricated using a nanoreplica molding process as described in previous work (see the previously cited patent literature in the Background) from a silicon grating template. Following replication of the grating structure, a $SiO_2$ layer with a thickness of ~300 nm (n=1.46) and a $TiO_2$ layer with a thickness of ~100 nm (n=2.25) were subsequently deposited over the grating surface by sputtering. The resulting PC slabs have a resonant reflection for the laser used to excite SERS ($\lambda$=600 nm, TE polarized (electric-field parallel to the grating lines)) at an incident angle of ~13°. Following PC fabrication, GLAD coatings of $SiO_2$ and Ag were applied using an electron-beam deposition system (Temescal) at a deposition rate of 5 Å/s for both materials. The angle between the incoming flux of evaporated material and the device surface was 5.0°. To minimize the shadowing effect of grating lines, the incoming flux was parallel to the grating sidewalls. The $SiO_2$ post layer was used to prevent quenching of resonant near-fields of the PC due to the high-loss metal structure. Since the resonance characteristic of the PC can be deteriorated by closely located metal nanostructures, a balance must be achieved between locating the Ag nanostructures too close to the PC surface while still positioning them within the PC evanescent field.

Figure 3B:
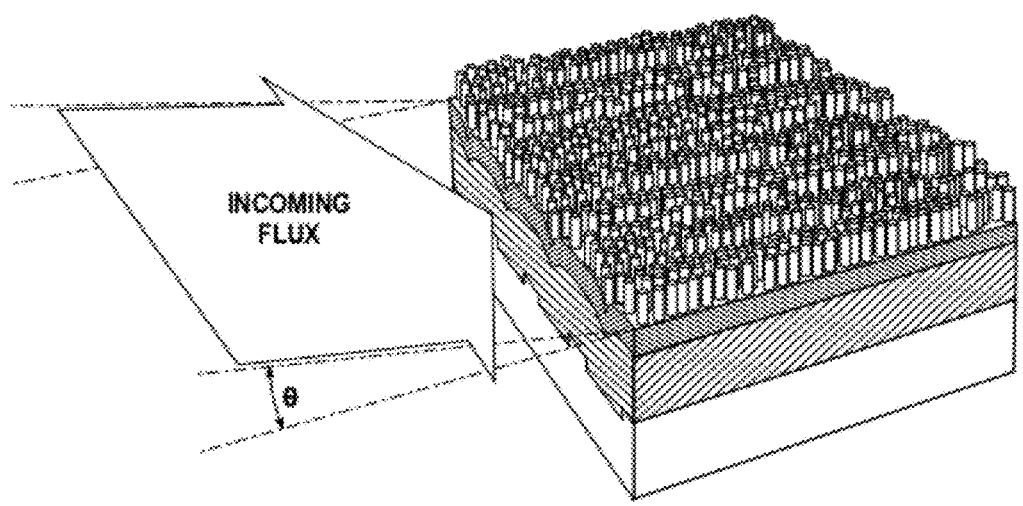
FIG. 3B is a schematic representation of the GLAD deposition process for producing the post-cap coating structure that results in ~30 nm isolated Ag nanoparticles on the PC surface.
Figure 3C:
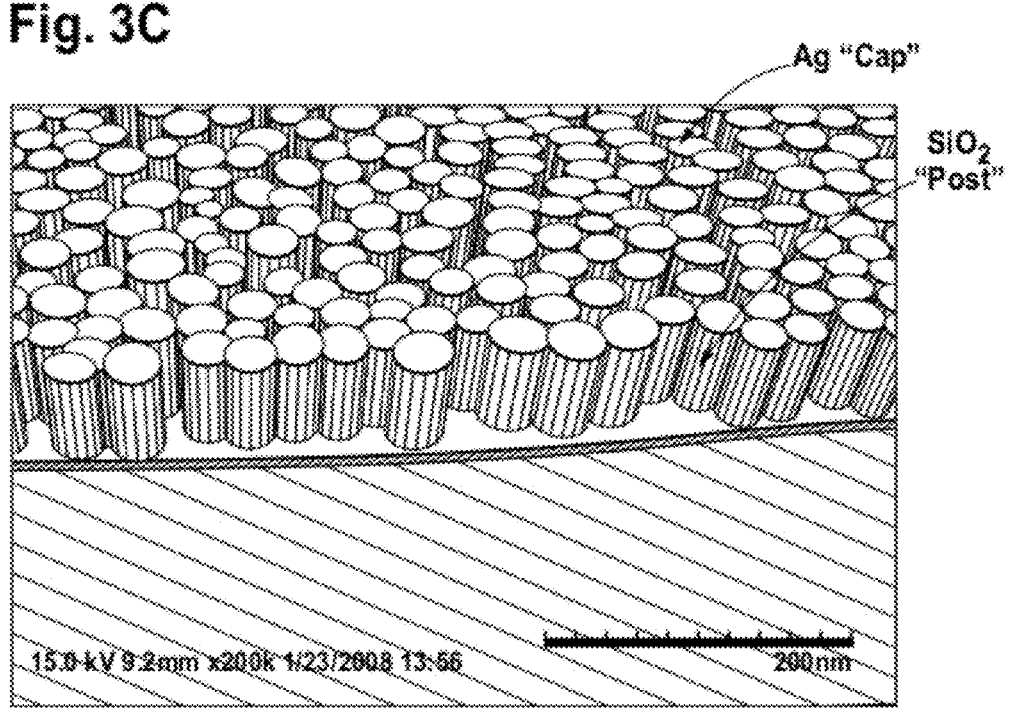
FIG. 3C is a SEM photo of the $SiO_2$—Ag post-cap structures produced by the GLAD method.
Figure 3D:
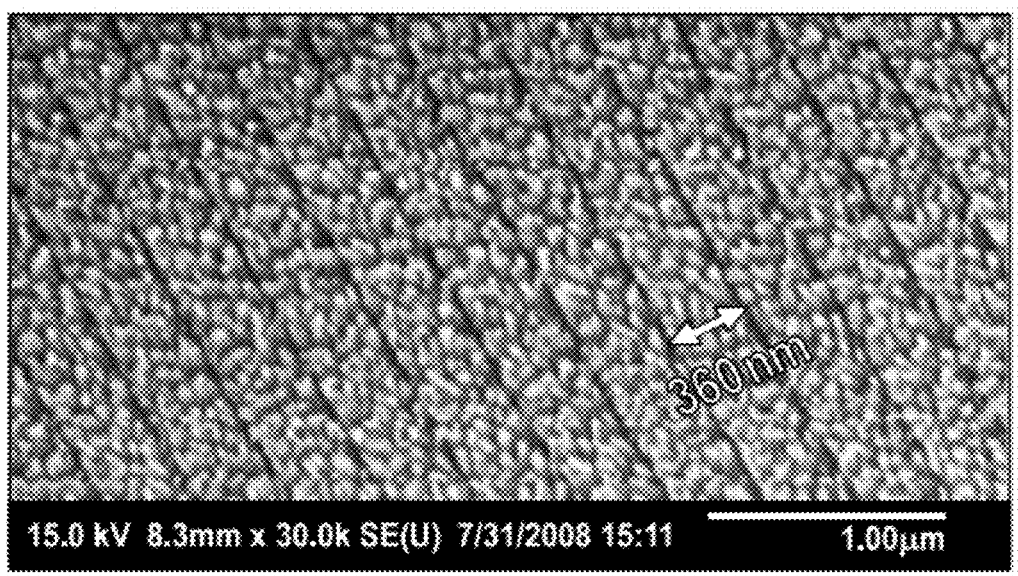
FIG. 3D is a SEM photo showing the structures deposited on the surface of a linear grating PC.

FIG. 3b shows the cross sectional scanning electron microscope (SEM) image of a $SiO_2$—Ag "post-cap" nanostructure with a $SiO_2$ thickness of 50 nm and Ag thickness of 30 nm, which was fabricated upon a silicon substrate for SEM imaging. Since the atomic mobility of Ag is larger than $SiO_2$, we obtained $SiO_2$—Ag "post-cap" structures in which the diameter of Ag regions is greater than the $SiO_2$ support post. For comparison, an ordinary glass slide with the $SiO_2$—Ag nanostructures was also prepared using the same GLAD process. FIGS. 3C and 3D are SEM images (top-view) of a PC-SERS substrate showing the post and cap structures at different scales.

Experimental demonstration of additional enhancement of PC-SERS was performed by measuring the Raman spectrum of trans-1,2-bis(4pyridyl)ethane (BPE) on the PC-SERS substrate, and by performing direct comparison with measurements from an ordinary glass substrate coated with the same $SiO_2$—Ag structure (GL-SERS substrate). The Raman detection instrument was comprised of a TE polarized Argon-dye laser excitation source (Coherent, INNOVA-90 and CR-500, $\lambda=600$ nm, output power=82 mW), a sample holder with a rotational stage, a power meter to measure laser transmittance through the sample, imaging optics, a spectrometer (SPEX-Triplemate), and a cooled CCD (Princeton Instruments). Raman scattered light was collected from a 235.4×51.8 $\mu m^2$ area, and the diameter of the laser beam spot was ~470 µm. A 2 µL droplet of BPE dissolved in methanol ($1\times10^{-4}$ M) was applied to each substrate by pipette. The BPE/methanol droplet spread out to form a circular region with a diameter of ~1.0 cm on the substrate, resulting in a density of ~$1.53\times10^{14}$ molecules/$cm^2$ and a number of exited molecules of 31 femto moles. For a laser wavelength of $\lambda=600$ nm, the PC resonance could be excited by illuminating at an angle of ~±13°, and precise tuning to the on-resonance condition for any substrate could be achieved by adjustment of the rotation stage to obtain a minima in laser transmitted intensity through the PC. Off-resonance conditions were obtained by detuning the incident angle from the transmission minima by ~±13°.

Figure 3E:
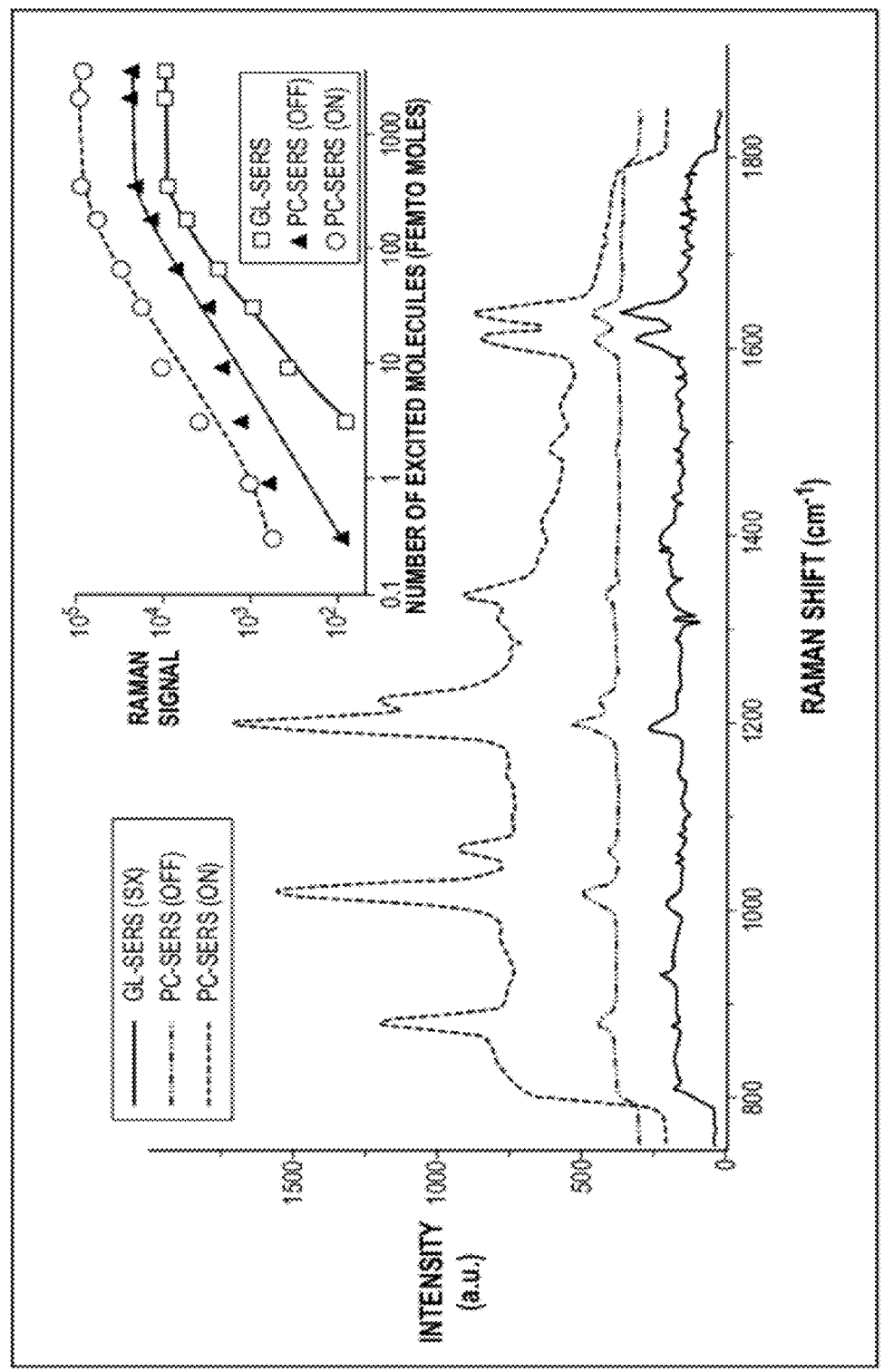
FIG. 3E illustrates PC-SERS detection results for BPE, comparing the measured SERS intensity for measurement with the excitation laser illuminating the PC structure at the resonant angle, illuminating the PC structure at an off-resonant angle, and on a glass substrate with the same post-cap structure, magnified 5× so its peaks may be seen. The inset shows the relationship between the SERS signal intensity at 1000 cm-1 as a function of BPE molecule density on the surface.

FIG. 3E shows the Raman spectra obtained from BPE using both GL-SERS and PC-SERS substrates at on/off resonance conditions. The spectrum for GL-SERS substrate was enlarged by a factor of 5. The Raman signal was defined as the integrated intensity of the 1200 $cm^{-1}$ peak after subtraction of the background signal. The Raman signals obtained from the GL-SERS substrate and the PC-SERS substrate at off- and on-resonance conditions were 531, 2762, 18702, respectively. Our results show that the Raman signal from the PC-SERS substrate increased significantly.

FIG. 3F compares the measured Raman signal and simulated $|E|^4$ (using Finite Difference Time Domain (FDTD) analysis) of the PC-SERS substrate for varying incident angles. The simulated $|E|^4$ are maximized at the resonance angles of ±13°, and at those incident angles, the Raman signal is also maximized. These results demonstrate that a PC-SERS substrate can substantially enhance SERS sensitivity and the enhancement factor was strongly correlated with the enhanced electric-field around the Ag nanostructure due to the PC guided mode resonance. A Langmuir analysis (signal vs. concentration) was also carried out to examine the additional enhancement effect attributable to the PC. The Raman signal from the GL-SERS substrate and the PC-SERS substrate at on/off resonance conditions are plotted against the estimated number of exited BPE molecules in FIG. 3E (top right). The response is nearly linear over three orders of magnitude (0.3~300 femto moles) after which there is saturation of the signal. The enhancement effect upon the Raman signal due to the guided mode resonance of the PC is observed throughout the entire concentration range, with an enhancement factor of 10-30× between GL-SERS and on-resonance PC-SERS.

The PC-SERS sensor of FIG. 3A-3D can be incorporated into simple clear plastic or glass tubing, flow cells and other devices, such as shown in FIGS. 1, 4, 5, 6, 7, 8 and 9 as described later in this document.

Example 3

Photonic Crystal (PC) Sensors Incorporated into Tubing

The photonic crystal sensors of U.S. Pat. Nos. 7,875,434, 7,148,94, 7,118,710, 7,094,595 and 6,990,259 can be incorporated into simple clear plastic disposable plastic or glass tubing, flow cells or other devices, such as shown in FIGS. 1, 4, 5, 6, 7, 8 and 9 and described later in this document. The instrumentation of the above patent documents can be used for detection of binding interactions occurring on the sensor surface. Depending on the capture molecules which may be present on the PC surface, the PC sensors could be used for detection of drug compounds, metabolite products, or bacterial pathogens.

3. Design and Modeling Considerations for Photonic Sensors Incorporated into Tubing DFB Laser Biosensors The DFB laser biosensor structure shown in FIG. 2a is shown as an exemplary model, although the precise dimensions and materials may be modified. The structure is comprised of a replica-molded linear grating (period=400 nm, depth=40 nm), coated with a thin film (300 nm) of Rhodamine 590-doped SUB, followed with a ~40 nm high refractive index coating of $TiO_2$. The structure shown in FIG. 2A was designed for excitation with a pulsed laser at $\lambda$532 nm, and vertically emitting laser output in the $\lambda=600$-625 nm wavelength output range, although other combinations of excitation wavelength and emission wavelength may be obtained by design. Grating lines are preferably oriented along the perimeter of the tubing (perpendicular to the direction of fluid flow) so the curling process will not modify the effective grating period. A major advantage of the active DFB laser sensor structure compared to passive optical resonant biosensors is that the excitation light need not be oriented at a precise coupling angle, and the emitted light will always emerge from the structure at a normal angle.

PC-SERS Sensors

The device structure described in FIG. 3a (period=360 nm, depth=60 nm) that produced a resonance with a $\lambda=600$ nm laser at an angle of 13 degrees in an air environment may be modified slightly to produce a resonance with a laser at $\lambda=785$ nm at normal incidence in a water medium. If both DFB laser biosensors and PC-SERS sensors are to be integrated within a single section of tubing and efficiently co-fabricated, the design goal would be to eliminate the $SiO_2$ buffer layer used in previous work, and to maintain the same (40 nm) grating depth as the DFB laser biosensor structure, so the nanoreplica molding master for both structures can be produced by the same etching process. The device period and $TiO_2$ coating thickness may be adjusted within this design constraint to achieve the desired resonance condition. While it would be desirable for the $TiO_2$ thickness for the PC-SERS sensor to be identical to that of the DFB laser, it is likely that the PC-SERS will require greater thickness (80-100 nm) to optimize sensitivity. Preliminary experiments in our lab also show that the "post-cap" dielectric-metal nanostructure (FIGS. 3A-3D) may also be modified for greater interaction with the PC resonant electric field when the metal is oriented like a nanofiber along the resonant electric field vector. Modifications of the GLAD deposition process for the metal nanostructures may be indicated to give greater enhancement. As with the DFB laser structure (FIG. 2B), the PC-SERS grating lines (shown best in FIG. 3B) are be oriented along the perimeter of the tube perpendicular to the direction of fluid flow.

PC Sensors

The PC sensors are constructed such that the lines of the grating are oriented along the perimeter of the tube, perpendicular to the direction of fluid flow.

4. Exemplary Tubing Embodiments and Manufacturing Considerations

FIG. 4 is a schematic diagram of the process used to produce a section of plastic biosensor tubing from a rectangular coupon. A replica molding process, as described herein in an in the background patent literature, is used to make a photonic sensor 400 on a thin, flexible plastic substrate, with an array of active areas 402 where the SERS nanodomes, PC grating or other photonic sensor surface is formed in the substrate. The photonic sensor is cut into a rectangular coupon 404 of the appropriate dimensions such that when the coupon is rolled into the form of a tube it will have the dimensions of interest. A jig 406 is formed with vacuum vent holes 410 and an inlet for receiving a air suction pipe 408. The sensor coupon 404 is placed or wrapped over the jig 406 and then suction air is applied to the pipe causing the sensor coupon 404 to be drawn snugly against the jig 406. Excess coupon material is trimmed from the jug and the seam between the ends of the coupon are sealed with an adhesive 412 to thereby form the coupon into a tube 414. The air suction is released and the tube 414 is removed from the jig. Barbed flexible plastic tubing connectors are inserted into the ends of the biosensor tubing 414 thereby permitting the tubing to be inserted in-line with biomedical tubing for in-line monitoring of metabolites, drug compounds or bacterial pathogens.

Figure 5:
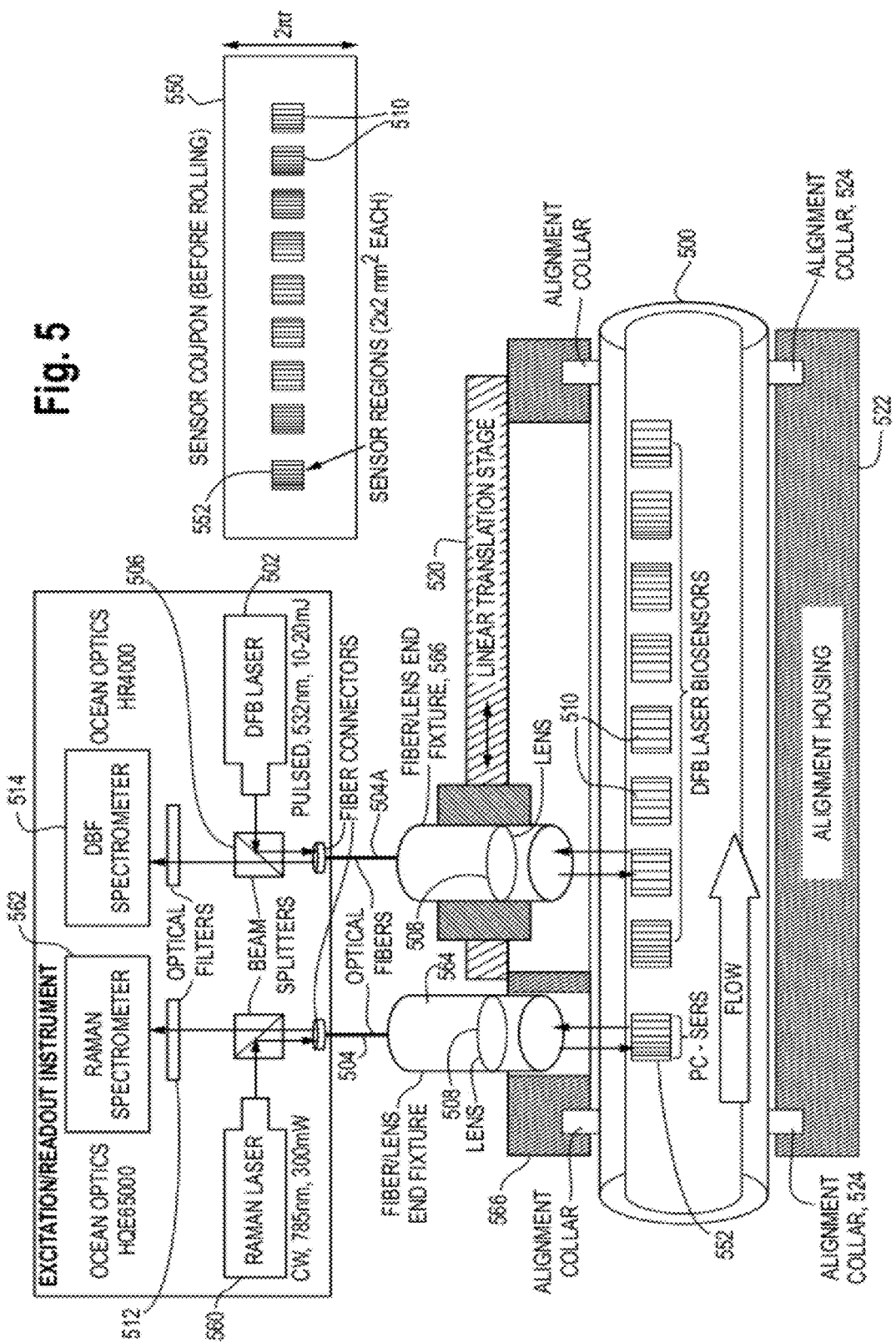
FIG. 5 is a schematic drawing of excitation/readout detection instrument and its interface with biosensor located in tubing. The detection head utilizes two optical fiber probes that align to their respective sensor regions (PC-SERS and DFB laser biosensor) using alignment collars on the tubing. The detection head incorporates a linear motion stage that enables the DFB head to sequentially scan an array of 8 biosensors. The detection head interfaces with detection instrumentation comprised of excitation lasers and spectrometers through optical fibers. The inset shows a sensor array fabricated as a rectangular coupon that allows individual DFB biosensor regions to be prepared with immobilized ligands for specific analytes before rolling into a tube format and installation within the tube, in a window formed in the tube or otherwise in fluid communication with the contents of the tube.

FIG. 5 is an illustration of another example of a biosensor coupon 550 having a number of sensor areas 510 and 552 arranged in an array. The manufacturing of the coupon 550 can be such that one of the sensor areas 552 is of a particular photonic sensor, such as a PC-SERS sensor, whereas the other sensor areas are of a different design, such as PC sensors or DFB laser biosensors. In the illustrated embodiment of FIG. 5, the coupon 55P has one sensor area or region 552 in the form of a PC-SERS nanodome sensor (described in detail below) whereas the remaining sensor areas 510 are DFB laser biosensors. The coupon 550 is rolled into a tube using the method of FIG. 4 and the biosensor tubing is placed in an alignment structure for purposes of reading the sensor as will be described in further detail in the instrumentation section of this document.

Figure 6A:
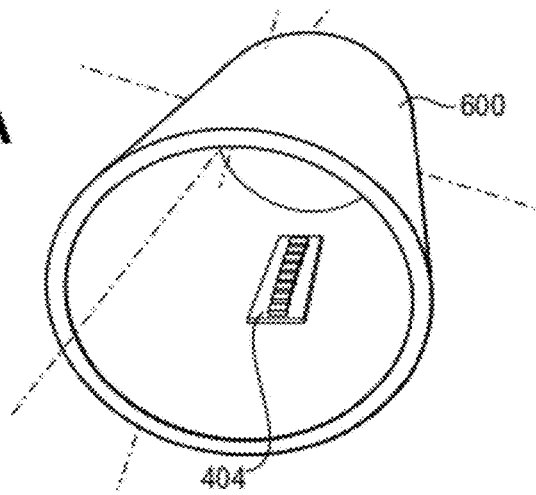
FIGS. 6A-6C are examples of tubing having photonic sensors formed or placed therein.
Figure 6B:
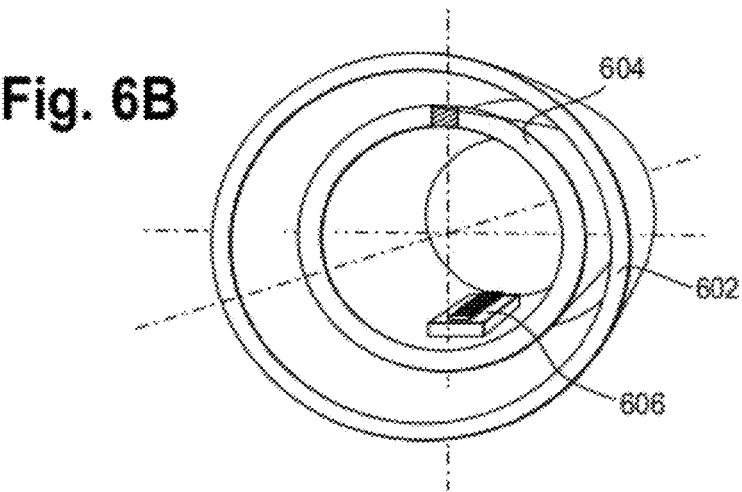
Figure 6C:
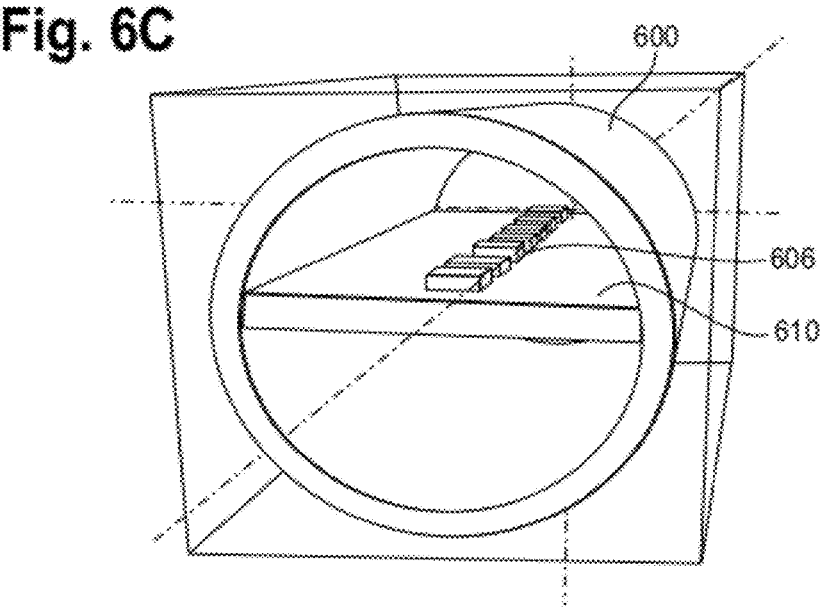

FIGS. 6A-6C show different arrangements of biosensors in tubing. In FIG. 6A, a section of tubing 600 (clear plastic or glass) has a sensor coupon 404 with an array of photonic sensor regions adhered or otherwise placed in the inner wall of the tubing such that the sensor active areas are in fluid contact with the contents of the tube 600. In one possible embodiment a window or hole is formed in the tubing 600 and the coupon is placed in the window and fixed in place with adhesive or otherwise. The tubing section containing the sensor is wrapped around existing tubing 600, with the existing tubing 600 having a hole such that the sensor region 404 is in fluid contact with the contents of the tube, as indicated in FIG. 6A. The sensor tubing segment of FIG. 6A is connected in series with ordinary plastic tubing using standard connectors.

In FIG. 6B, an outer tube 602 of clear plastic or glass has an inner tube 604 having a photonic sensor 606 formed therein, e.g. manufactured using the method of FIG. 4. The inner tube 604 can be affixed against the wall of the outer tube such that the photonic sensor 604 is in contact with the wall of the outer tube 602 enabling the detection instrument to direct light on the sensor 606 and obtain readings from the sensor. In FIG. 6c, the photonic sensor 606 is manufactured using the nanoreplica molding process and then placed on a support 610 which is inserted into the tube.

FIG. 7 is another example of a PC-SERS photonic sensor incorporated into tubing, and related instrumentation. In FIG. 7, the PC-SERS photonic sensor is formed into a tube 704 using the method of FIG. 4. The sensor tubing 704 is connected in series with medical tubing 700 and 706 using standard tubing connectors 702. An in-line fluid identification system or instrument 710 is provided, including a laser light source 712, optical fiber 714 carrying laser light to an objective lens 716 which directs light on the sensor area of the sensor tubing 704. Reflected light from the sensor area in the tubing is collected via the lens 716 and focused on an optical fiber 718 which carries the light to a spectrometer 720. The spectrometer produces Raman spectra 722 of metabolites or drub compounds present in the tubing.

FIG. 8 is an example of a flow cell 800 having a PC-SERS nanodome sensor 802 for monitoring the compounds present in the flow through the cell. The flow cell is connected to an inlet tube 806 and an outlet tube 808. The nanodome sensor 802 is placed on the lower surface of a clear glass window 804 that covers the interior of the flow cell, thereby placing the sensor in fluid communication with the contents of the flow cell. Laser light from a detection instrument (not shown in FIG. 8) is carried by an optical fiber which directs the light onto the flow cell and captures the reflected light from the sensor back to the instrument.

Figure 9:
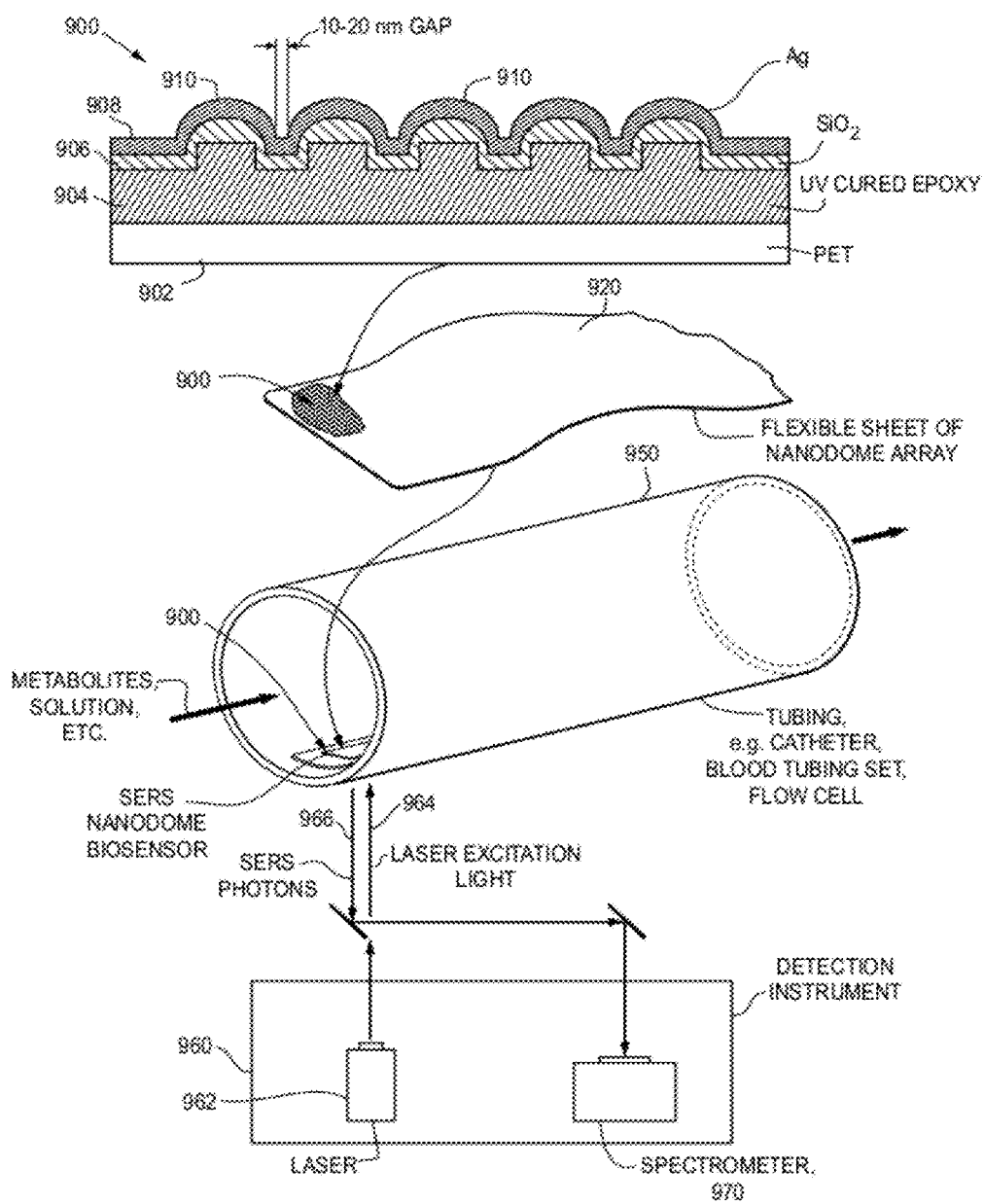
FIG. 9 is an illustration of a PC-SERS nanodome sensor formed on a flexible plastic sheet or film which is placed within a piece of tubing and the associated detection instrumentation.
Figure 10A:
FIG. 10 is an illustration of the process of forming the PC-SERS nanodome sensor of FIGS. 8 and 9.
Figure 10B:
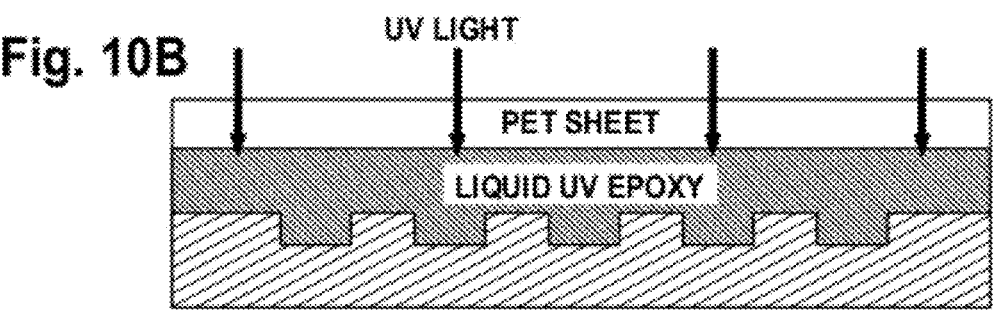
Figure 10C:
Figure 10D:
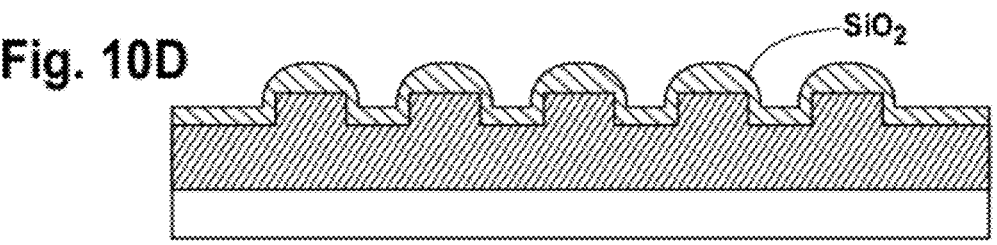
Figure 10E:
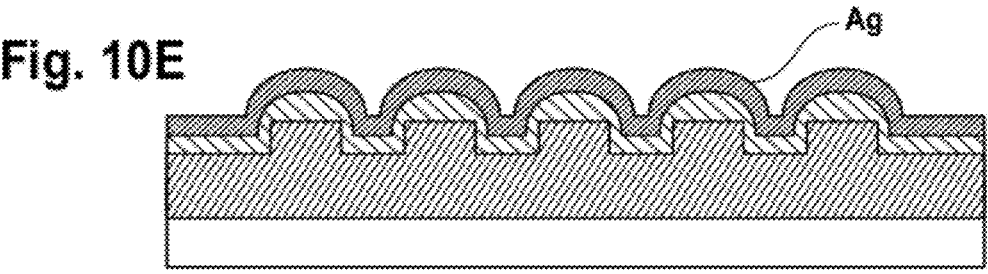

FIG. 9 is another example of a PC-SERS nanodome sensor in the form of a PET clear flexible plastic substrate 902, a UV cured epoxy grating layer 904 with periodic high and low regions, a $SiO_2$ layer 906 deposited on the grating layer, and a silver layer 908 deposited on the $SiO_2$ layer 906 to thereby form an array of nanodomes 910 having a separation between the domes of approximately 10-20 nm. The nanodome sensor 900 of FIG. 9 is manufactured as a flexible sheet of nanodomes which is then placed into the interior of a clear plastic or glass tube 950 for in-line monitoring of metabolites, drug compounds or other substances. The sensor 900 includes a detection instrument 960 having a laser light source 962 which directs laser light 964 onto the sensor 900 within the tubing and emitted SERS photons from the sensor are collected (via optical fiber) and directed to a spectrometer 970 in the detection instrument 960.

The SERS nanodome sensor of FIG. 9 can be used in liquid-containing structures generally, such as flasks, test tubes, beakers, flow cells, and the like. Alternatively, the SERS nanodome sensor of FIG. 9 can be incorporated into a testing format, such as a glass microscope slide, in which the sample is in an air environment.

Although the SERS surfaces are precisely engineered to incorporate a high density of electromagnetic hot spots, they are fabricated over large surface areas on flexible plastic substrates using processes that will enable these devices to be formed into convenient sections of tubing (as shown in FIG. 4) or simply wrapped around the outer diameter of ordinary biomedical tubing (e.g. FIG. 1) in which a hole in the tubing allows exposure of the SERS surface to the tubing contents.

Further Manufacturing Considerations a. Sensor Form Factor

As shown in FIG. 5, the DFB, PC and/or PC-SERS structures may be co-fabricated upon a single sensor rectangular "coupon" that contains 1 PC-SERS device, and a linear array of say 8 DFB devices, or say 6 or 8 PC sensors. Alternatively, the sensor formats may be fabricated in an array with only one sensor type within a section of tubing. For compatibility with typical catheter tubing, one would fabricate sensor tubing with inside diameters between 1 mm and 5 mm. In this case, each sensor would be comprised of an approximately 2×2 $mm^2$ grating area, with 1 mm spaces between adjacent sensors. Therefore, the sensor regions will require ~27 mm of tubing length. It is possible to add ~25 mm of "blank" tubing length to the sensor coupon in the upstream and downstream directions to leave sufficient room for alignment collars and tubing connectors, so the total length of the coupon would be increased accordingly. The width of the sensor coupon would be 3.14 mm (for 1 mm diameter tubing) or 15.71 mm (for 5 mm diameter tubing).

b. Nanoreplica Molding

A negative surface image of the desired grating structures for the DFB and PC-SERS devices is produced in a Si wafer using electron beam lithography and standard reactive ion etching to produce a "master" mold structure. The master wafer is used as a mold template to produce the grating structures in a UV-cured polymer material, as described in Preliminary Results. However, instead of using a PET substrate, substrate materials such as polyurethane and nylon sheets, that are typically used in medical tubing may be used instead. These substrates must be thin enough for curling into tubing, yet mechanically robust enough to withstand fabrication processes. Therefore, the thin substrate will be attached to a "backing" polyester film with a temporary laminating adhesive that will be peeled away before the curling process.

c. DFB Laser Biosensor

The DFB sensor fabrication will be performed as described in previous publications, but the DFB structures will be shielded from the PC-SERS post-cap nanostructures in the GLAD process through the use of a mechanical shadow mask. The same mask will be used to enable greater $TiO_2$ thicknesses to be deposited only on the PC-SERS structures, as needed.

d. PC-SERS

A photolithography mask will be used to prevent curing of the dye-doped SU8 film on the PC-SERS region, so it may be selectively removed. All other process steps will be similar to those described earlier in this disclosure and in previous publications.

4. Tube Forming

One method for fabricating biosensor tubing is described as follows: The sensor coupon will be formed into a section of tubing by rolling the sensor around a cylindrical pre-form (with the sensors on the inside surface) and joining/sealing the two ends together, as shown in FIG. 4 and described above. A fixture is manufactured that allows the sensor coupon to be wrapped around a cylinder, held securely during the seam sealing process, and release without damaging the sensor structure. Currently, we envision using a hollow aluminum, Teflon-coated cylinder with a diameter equal to the desired tubing inside diameter. The cylinder will be hollowed out, and contain numerous vacuum holes along its length and perimeter that will hold the sensor in place. A seam forming the coupon into a tube is sealed using adhesive, heat lamination, or laser lamination. After seam sealing, the vacuum will be released, and the pre-form will be withdrawn from the tubing. Injection of air or fluid pressure into the pre-form may be used to facilitate release.

Alignment Collars

As shown in FIG. 5, two alignment collars (in the form of rubber o-rings) are cemented in place in designated locations on the upstream and downstream sides of the tubing. The purpose of the alignment collars is to allow the tubing to be positioned accurately within the detection instrument.

Additional Manufacturing Methods i. Adhere Small Sensor Inside Tube

The sensor may be fabricated upon a flat substrate, and small sections of sensor (for example <2×2 $mm^2$) may be cut out from the substrate. If one edge of the sensor rectangular sections is smaller than the inside diameter of the tubing, the sensor may be physically inserted within the tubing, and then attached to the interior wall of the tubing with adhesive. In this case, the sensor substrate must be thin enough not to substantially alter the cross sectional area of the tubing, and the tubing must be optically transparent to allow illumination of the sensor and collection of the reflected, emitted, or scattered light. Ideally, the sensor would be attached to the inner surface of the tubing in such a way as to conform to the inner surface, resulting in the sensor adopting a concave shape after attachment. Alternatively, a sensor could be attached with adhesive to a second, larger, piece of flexible plastic material, in which the second substrate is rolled to form a cylindrical tube, with the sensor attached inside. See FIG. 6B.

ii. Cut Window in Tube

In this case, a section of rigid tubing would be prepared with an opening cut into it, to expose the inner surface. The opening could be prepared to precisely match the rectangular dimensions of a flat section of sensor substrate, that would fill the opening and be sealed with adhesive. See FIG. 6A. Alternatively, the tubing could be cut in such a way as to leave flat regions upon which the sensor may be attached with adhesive. The cut in the tubing would expose the inner surface of the tubing, and the sensor would cover the opening and the flat regions simultaneously. This configuration would ideally require tubing with thick walls, and mechanical rigidity, but would not require the tubing to be optically transparent. Tubing sections with an exposed inner surface may be produced inexpensively by injection molding or by machining ordinary cylindrical tubing. An advantage of this method is that the sensor may be maintained in a flat state for simplified measurement. A further advantage is that the rigid tubing may be held securely within a detection instrument.

iii. Insert Rolled Film/Sensor Structure into Tube

In a similar fashion to method no. 1 above, a section of sensor substrate may be rolled and placed into a tubing with a larger inside diameter, as shown in FIG. 6B.

iv. Insert Sensor into the Middle of Shrinkable Tube.

A section of sensor substrate may be placed on a support and inserted into a section of tubing, so as to remain flat and to occupy space in the center of the tube, as shown in FIG. 6C. This configuration would require transparent tubing and transparent fluid media. The sensor would be fabricated upon a rigid substrate or support (e.g., glass), so as to maintain a flat state when inserted within the tubing. Adhesive may be used to hold the sensor in place.

Alternative tubing/sensor integration and fabrication methods are also possible, although rolling a rectangular sheet of material to form a tubing section may be the lowest cost method for fabricating biosensor tubing. See FIG. 4.

Any of the above methods may be applied to the inner surface of liquid containing vessels generally, e.g., flow cells, test tubes, beakers etc.

5. SERS Nanodomes and Use Thereof in Tubing, Flow Cells and Similar Arrangements A currently preferred embodiment for a photonic sensor incorporated into tubing takes the form of a Surface-Enhanced Raman Scattering nanodome sensor in the form of an array of closely spaced metal nanodomes fabricated on a flexible plastic film. The nanodome sensor, and methods of fabrication, are described in further detail below.

In brief, the SERS metal nanodome sensor takes the form of a periodic grating structure (e.g., UV-cured epoxy) bonded to a substrate (such as clear plastic, e.g. PET or MYLAR™)

using a nanoreplica molding process. The sensor design is shown in FIG. 9 and described previously.

A material 906 such as SiO2, the choice of which is not especially critical, is deposited on the periodic grating structure 904 to provide a periodic array of dome structures. A metal thin film coating 908 is deposited on the material, e.g., using electron beam evaporation. In one possible embodiment, the metal thin film coating is in the form a coating of silver or gold of between 5 and 100 nm in thickness. The spacing between the metal nanodomes in the arrays is between approximately 10 and 30 nanometers in a representative embodiment, and more preferably between 10 and 20 nm.

FIG. 10 shows an exemplary manufacturing method for producing SERS nanodome sensors. First, nanoimprint lithography (NIL) (Molecular Imprints) and reactive ion etching was used to pattern an 8-inch (200 mm) diameter silicon wafer with a 2-dimensional array of 300 nm diameter holes (period=400 nm, depth=130 nm), in 8×8 mm2 dies to produce a mold template with overall feature dimensions of 120×120 mm2. The completed silicon mold template was subsequently treated with dimethyl dichlorosilane (GE Healthcare) to promote clean release of the replica (FIG. 10a). Next, a negative volume image of the silicon surface structure was replicated onto a flexible polyethylene terephthalate (PET) substrate by distributing a layer of liquid UV curable polymer (Gelest Inc.) between the silicon wafer and the PET substrate. The liquid polymer conforms to the shape of the features on the wafer, and is subsequently cured to a solid state by exposure to a high intensity UV lamp (Xenon Inc.) at room temperature (FIG. 10b). After curing, the molded structure was released from the wafer by peeling away the PET, resulting in a polymer replica of the silicon wafer structure adhered to the PET sheet (FIG. 10c). The replica molding process results in the formation of a rectangular array of ~130 nm-tall polymer cylinders that are separated by ~100 nm at their outer perimeters. In order to produce a SERS active surface with metal nanostructures that are separated by distances smaller than 100 nm, SiO2 was applied over the polymer cylinders by electron-beam evaporation (FIG. 10d). Through control of the deposited SiO2 thickness (SiO2 films of 0, 50, 75, 100, and 125 nm were investigated), the cylindrical polymer surface evolves into a dome structure with a radius that increases with SiO2 thickness. SiO2 deposition is followed by application of a 200 nm silver thin film by electron beam evaporation to complete the device (FIG. 10e).

The nanoreplica molding process can be performed over relatively large areas and the areas cut up into individual sensors, e.g., an area of 120×120 mm$^2$ and then cut into sensors of a desired dimension for the tubing, flow cell, or other fluid containment device of interest.

Figure 11A:
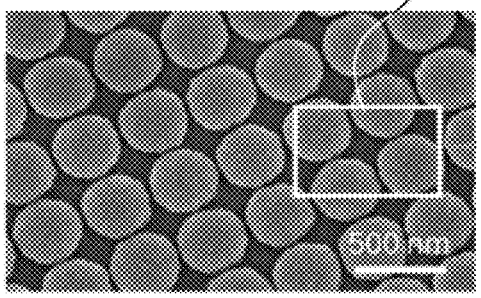
FIGS. 11A-11F are SEM images of nanodome array substrates.
Figure 11B:
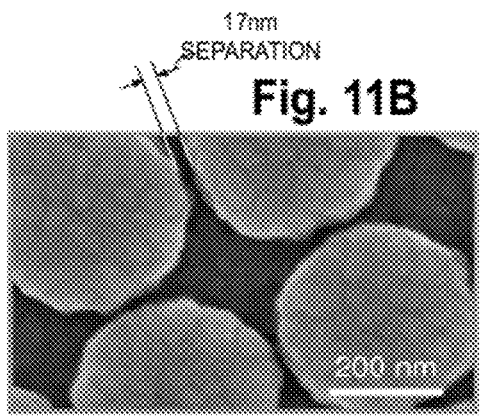
Figure 11C:
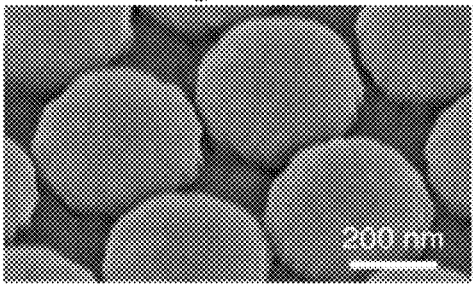
Figure 11D:
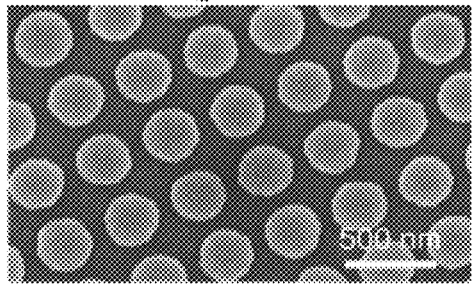
Figure 11E:
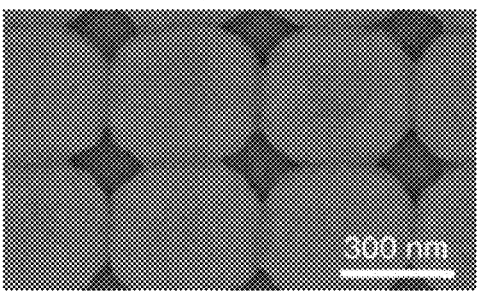
Figure 11F:
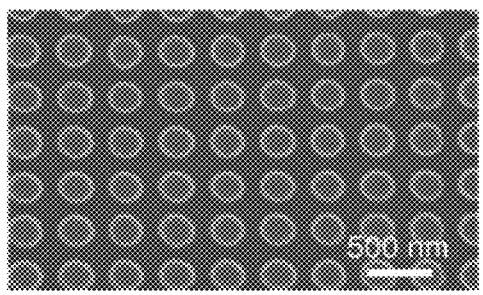

The SiO$_2$ thickness was used to control the nanodome separation distance, which is the most important variable for determination of the SERS enhancement factor. Scanning electron microscope (SEM) images of the fabricated SERS substrates are shown in FIGS. 11A-11F. The SEM images were used to measure the separation distance between adjacent domes. For SiO$_2$ thicknesses of 0, 50, 75, 100 nm, the separation distance for the nanodome arrays were 84, 59, 33, and 17 nm with the nanodome base diameters of 311, 344, 363, and 377 nm, respectively. We found that when the SiO$_2$ thickness exceeded 100 nm, the dome spacing reduced to zero, resulting in domes that touch each other, as shown in FIG. 11(e). SEM measurements confirmed that the replica molded structures have a period of ~400 nm, as would be predicted by the period of the silicon mold template.

In preferred embodiments, the spacing between the metal nanodomes and the periodicity of the metal nanodomes in the array is such that a resonance is created near to or at the wavelength of a laser of an instrument interrogating the biosensor and exciting SERS phenomena in the sensor. The key to good performance is managing to get a tiny (~10 nm) gap between adjacent domes while choosing a nanodome period that gives a resonant wavelength that matches the excitation laser wavelength. Preliminary results suggest that by constructing the nanodome sensor in this manner yields an additional order of magnitude in sensitivity of the sensor. Presently preferred separation distances are between 10 and 30 nm with 10-20 nm being more preferred.

Figure 17:
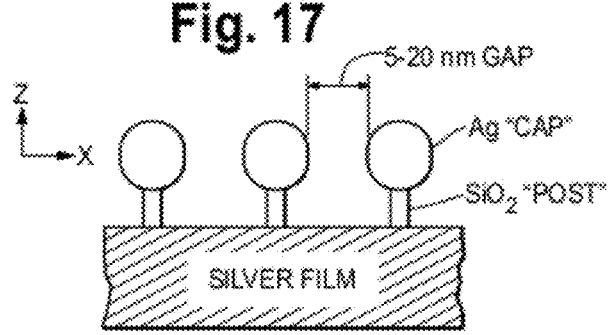
FIG. 17 is a cross-section of a nanodome PC-SERS sensor in which the sensor has a post-cap structure.
Figure 18:
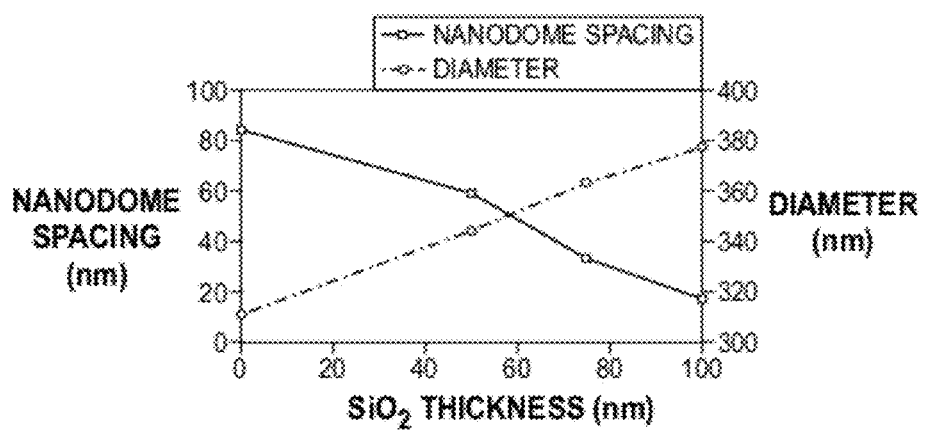
FIG. 18 is a plot of the measured nanodome separation distance (squares, left axis) and diameter (circles, right axis) as a function of SiO2 thickness deposited on the replica.

FIG. 17 shows an alternative construction of the SERS nanodome sensor in which SiO2 "posts" are deposited on a silver film substrate and an Ag "cap" or dome structure is deposited on the silver posts, resulting in an Ag nanodome array with a separate between the domes of between about 5 and 20 nm.

Since the discovery of the SERS phenomenon, two main enhancement mechanisms have been proposed: the chemical enhancement effect and the electromagnetic enhancement effect. Of the two mechanisms, it is believed that the SERS enhancement is dominated by the electromagnetic mechanism, which is due to the enhanced electromagnetic fields originating from the localized surface plasmon resonance (LSPR) effect on both the incident laser and the Raman scattered radiation from the analyte molecules on metal nanostructures. The theoretical SERS enhancement has been described by the following expression $$EF_{SERS} \propto \frac{|E_{loc}(\omega_{ex})|^2}{|E_0(\omega_{ex})|^2} \frac{|E_{loc}(\omega_s)|^2}{|E_0(\omega_s)|^2} \quad \text{Equation 1}$$

where $E_{loc}(\omega_{ex})$ is the amplitude of the enhanced local electric field at the laser excitation frequency, $E_0(\omega_{ex})$ is the amplitude of the incident electric field (provided by the laser) at the laser excitation frequency, $E_{loc}(\omega_s)$ is the amplitude of the enhanced local electric field at the Raman scattered frequency, and $E_0(\omega_s)$ is the amplitude of the electric field at the Raman scattered frequency (radiated by the analyte molecules).

Figure 19A:
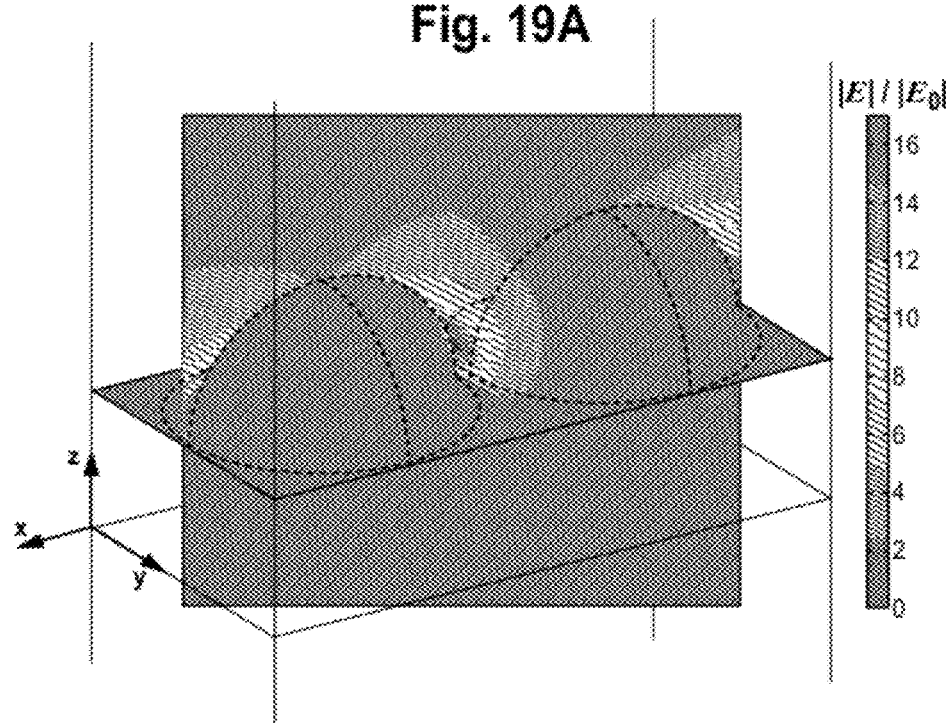
FIG. 19(a) is a 3-D FEM simulation of the electric field distribution around the Ag nanodome in a PC-SERS nanodome photonic sensor. The scale bar on the right side represents the normalized amplitude of the scattered electric field with respect to the incident electric field amplitude. The nanodome arrays were excited with an incident plane wave at λ=785 nm, propagating in the −z direction with linear polarization in x direction. The nanodome array was modeled as a dimer structure with symmetric boundary conditions on the sidewalls of the simulation boundary.
Figure 19B:
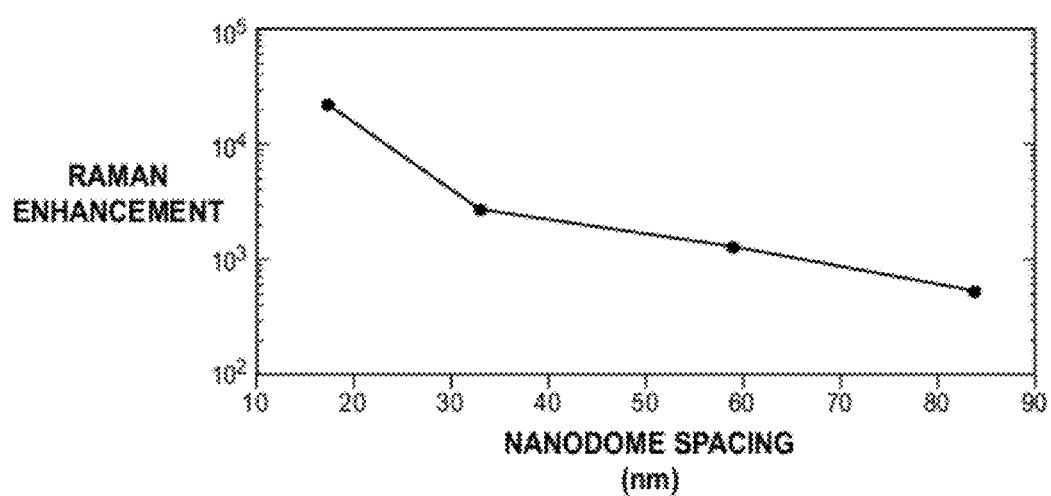
FIG. 19(b) is a plot of the maximum Raman enhancement calculated from the FEM simulation of electric field distribution around the nanodome array for the laser excitation (λ=785 nm) and the Raman scattered wavelength corresponding to wavenumber shift of 1370 cm-1 for inter-dome separation distances of 17, 33, 59, and 84 nm.

In order to investigate the characteristics of the nanodome array structure as a SERS substrate and to study the effect of inter-dome separation distance on the SERS enhancement (Equation 1), finite element method (FEM) modeling using a commercially available software package (COMSOL Multiphysics) was utilized to map the electric field distribution around the nanodomes. The result of the 3-D simulation of the electric field distribution between two adjacent nanodomes within the array is shown in FIG. 19A with the scale bar on the right side representing the normalized amplitude of the scattered electric field with respect to the incident electric field amplitude. The regions of enhanced electric field are clearly visible in the area between adjacent nanodomes where the separation distance is minimum, as expected due to the coupling effect of LSPR field enhancement. To approximate the conditions in our measurement apparatus, the nanodome arrays in the simulation were excited with a normally incident plane wave at λ=785 nm, propagating in the −z direction with linear polarization in x direction. The simulation was performed by approximating the metal-coated nanodome structure as a hemisphere. The nanodome array was modeled as a dimer structure with symmetric boundary conditions on the sidewalls of the simulation boundary, in order to reduce the computational load. FIG. 19b shows the maximum values of Raman enhancement calculated using Equation 1 from the FEM modeled electric field distribution for the laser excitation and the Raman scattered wavelength corresponding to wavenumber shift of ~1370 cm-1 for nanodome arrays of inter-dome separation distances of 17, 33, 59, and 84 nm, to match the spacing measured by SEM. Note that the enhancement factor increases for nanodome separation below about 33 nm.

Figure 20:
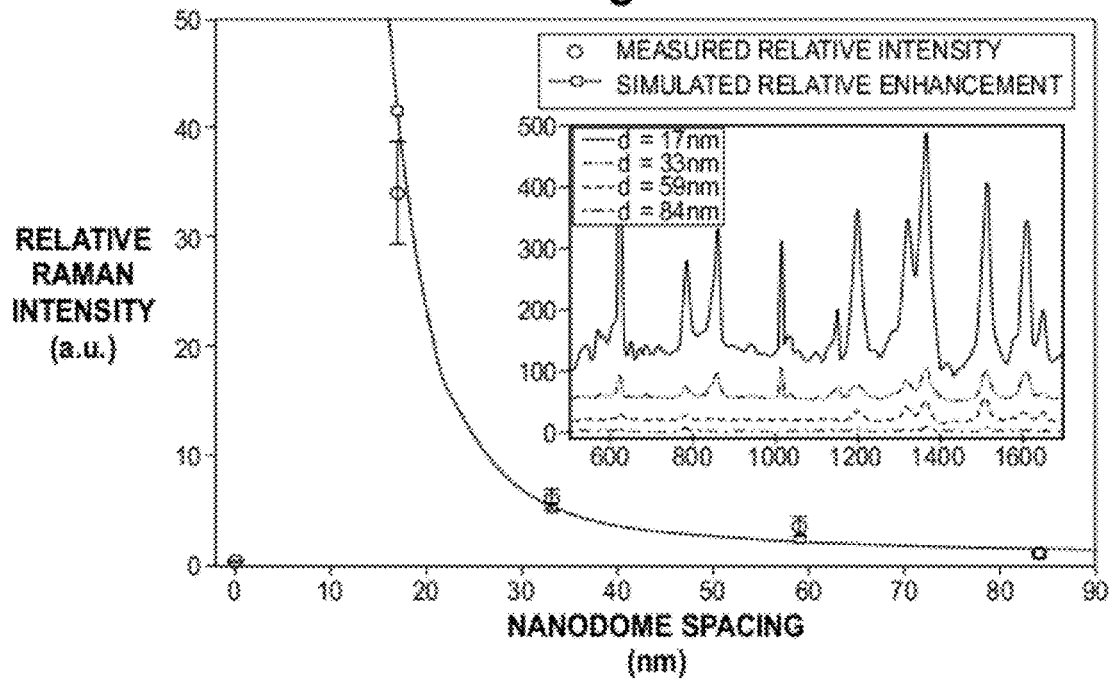
FIG. 20 is a plot of relative SERS intensity (I(d)/I($d_{max}$=84 nm)) as a function of nanodome separation distance, d, for 1 μM R6G, measured at the Raman peak corresponding to a 1370 $cm^{-1}$ wavenumber shift. Experimentally measured relative SERS intensity are marked as hollow dots with error bars representing ±1 standard deviation for five measurement locations throughout the nanodome array substrates for each dome separation distance (n=5). Relative SERS enhancement values obtained from the FEM simulation are plotted as squares. The inset shows example SERS spectra for the nanodome array substrates with nanodome spacing ranging from 17 to 84 nm.
Figure 21:
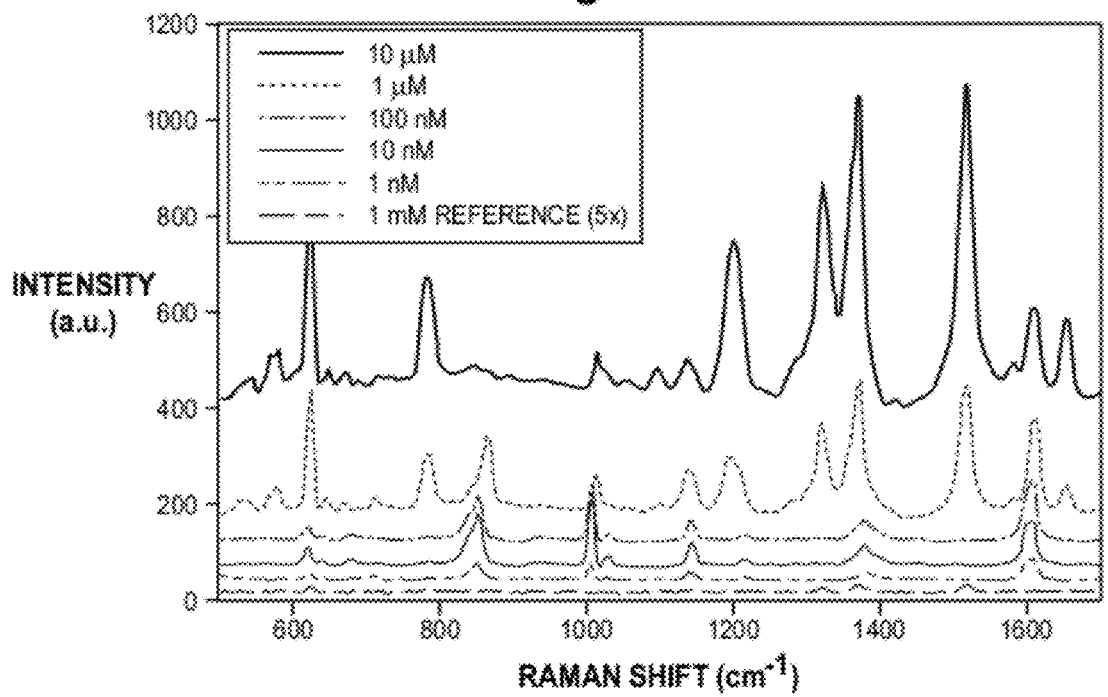
FIG. 21 is a plot of SERS spectra of R6G molecules ranging from 1 nM to 10 μM on a PC-SERS nanodome array substrate with d=17 nm and 1 mM R6G on the reference surface without the nanodome array. The reference spectrum was multiplied by a factor of 5 in the plot).

In order to experimentally verify the effect of nanodome spacing on SERS intensity, 1 μM Rhodamine 6G (R6G) solution was applied to each substrate. The Raman measurement was performed using a 30 mW laser operating at λ=785 nm, which was focused on the substrate surface by a 10× objective lens (NA=0.28), resulting in a probe spot radius of 10 μm. SERS photons were collected by the same objective lens, into a spectrometer (Princeton Instruments) comprised of a SP2300i monochromater and a PIXIS 400 CCD (1340×400 pixel array) using an integration time of 1 sec. The collected SERS signals were processed using a multi-polynomial fitting method to remove background, and a Butterworth low-pass filter to remove noise. The experimentally measured relative SERS intensity, defined as $I(d)/I(d_{max})$ where $d_{max}$=84 nm, of the substrates as a function of nanodome separation distance d plotted as hollow dots is shown in FIG. 20. The SERS intensity values were measured at a Raman peak corresponding to a wavenumber shift of 1370 cm$^{-1}$. The error bars in the figure represent ±1 standard deviation of the relative intensity obtained throughout five measurement locations throughout the nanodome array substrates for each inter-dome separation distance. FIG. 20 shows the FEM-simulated relative SERS enhancement values with respect to the nanodome spacing marked as red squares. As shown in FIG. 20, SERS intensity/enhancement dependence on inter-dome spacing shows a very good agreement between the experimentally measured and simulated values. The inset in FIG. 20 shows example SERS spectra for devices with different separation distances ranging from 17 to 84 nm. The SERS intensity observed from the experiment demonstrates that SERS enhancement is very sensitive to inter-dome spacing, and suggests that even higher enhancements may be achievable by controlling the spacing below 17 nm. Interestingly, when adjacent nanodomes are allowed to touch each other (d=0 nm), the enhancement abruptly drops down to the same value obtained when the inter-dome spacing is large. This suggests that the majority of the enhancement comes from the "hot spot" region located in the volume between adjacent nanodomes with enhanced electromagnetic field intensity from inter-dome near-field interaction, consistent with the electric field distribution obtained In order to experimentally measure the SERS enhancement factor for the nanodome array substrates, a concentration series of R6G molecules (1 nM-10 μM) were deposited on a SERS sensor surface with an inter-dome separation distance of d=17 nm. 1 mM R6G was also deposited on the same substrate in the area outside of the nanodome region to serve as a reference. Using the same detection instrumentation and measurement parameters outlined previously, the SERS spectra shown in FIG. 21 were obtained.

The experimentally measured enhancement factor (EF) for a SERS system is given as $$EF_{SERS} = \frac{I_{SERS}/N_{surf}}{I_{ref}/N_{bulk}} \quad \text{Equation 2}$$

where $I_{SERS}$ is the surface enhanced Raman intensity, $N_{surf}$ is the number of molecules within the enhanced field region of the metallic substrate contributing to the measured SERS signal, $I_{ref}$ is the Raman intensity from the reference region, and $N_{bulk}$ is the number of molecules within the excitation volume of the laser spot for the analyte on the reference region. $N_{bulk}$ was calculated by the following equation $$N_{bulk} = \pi r^2 h c N_A \quad \text{Equation 3}$$

where r is the radius of the excitation laser spot (10 μm), h is the thickness of the R6G spot on the reference region (0.72 μm), c is the molar concentration of the R6G analyte on the reference region (1 mM), and $N_A$ is the Avogadro's number. $N_{surf}$ was defined to be the number of molecules occupying the volume of the hot spot region with high enhancement of the local electric field. The volume of the hot spot region for calculation of $N_{surf}$ was determined from the FEM simulation of the electric field distribution where the enhanced signal was assumed to take place within the volume bounded by which the exponentially decaying enhanced electric field away from the hot spot region is reduced by a factor of 1/e. The electric field amplitude plot along y and z direction through the maximum were fitted to an exponential decay function to obtain the 1/e distance along the y and z direction. For the distance in the x direction, the average distance between adjacent domes at 1/e values in the z direction was used, approximating the curvature of the dome to be linear. Using the volume fraction of the hot spot and the SERS intensity from the 1370 cm$^{-1}$ peaks of 1 nM R6G on the SERS active region and 1 mM R6G on the reference region for $I_{SERS}$ and $I_{ref}$, respectively, the SERS EF was calculated to be 1.37× 10$^8$. The preceding calculation of enhancement factor describes only the enhancement that occurs within the region of highest electric field, and does not account for the fact that only a portion of the available surface area of the substrate is supporting an elevated electric field. To take into account the volume density of hot spots, the spatially averaged EF can also be calculated. For spatially averaged EF, all analyte molecules within the excitation laser spot volume are assumed to contribute equally to the measured SERS signal, so the volume fraction of enhanced field region is not considered for the calculation. The spatially averaged EF, which represents an underestimation of the local EF from Equation 2, provides a more practical, experimentally measured value of the SERS enhancement. The spatially averaged EF of the Ag nanodome array substrate was calculated to be 3.16×10$^6$.

In summary, we have demonstrated a SERS substrate consisting of closely spaced array of metal-coated dielectric nanodomes fabricated utilizing a low-cost, large-area nanoreplica molding method, in which the inter-dome spacing is precisely controlled through the thickness of SiO2 and Ag thin films deposited over a replica molded array of polymer cylinders. FEM simulation can be used to investigate the electromagnetic field distribution between adjacent nanodomes, where excellent agreement between the experimentally measured and simulated values for the intensity/enhancement dependence on inter-dome spacing was obtained. Experimentally measured SERS enhancement factor of 1.37×10$^8$ was demonstrated for the SERS substrate presented above. The nanoreplica molding process allows simple, low-cost fabrication of the required surface features over a large area, providing a path towards mass production of SERS substrates with high enhancement factor suitable for many applications, including in tubing flow cells and other fluid containing devices.

Example 5

Nanodome Photonic Sensor Incorporated into Flow Cell for Urea and Metabolite Detection For SERS surfaces to be viable for an application in which they would be used as a single-use disposable point-of-care sensor, it is necessary to provide a structure that simultaneously provides a large electromagnetic enhancement factor and is made using a low-cost, large-area manufacturable fabrication method. The SERS nanodome sensor used in the present disclosure provides label-free identification/detection of analytes without having to immobilize probe molecules on the sensor surface. The nanodome surface used in the present study is produced on a flexible plastic substrate by a large-area nanoreplica molding process to provide peak enhancement factors of $1.37 \times 10^8$. The exemplary experiments on the detection of promethazine and urea demonstrate the clinical potential for SERS sensors incorporated within biomedical tubing. The system could enhance patient safety through prevention of drug delivery errors that occur by administering an incorrect drug or an incorrect dose, and provide more timely information on the status of a patient through monitoring of metabolite.

a. Nanodome Sensor Fabrication—Nanoreplica Molding Process

To produce a template used for the molding, nanoimprint lithography (Molecular Imprints) and reactive ion etching were used to pattern an 8-inch (200 mm) diameter silicon wafer with a 2-dimensional array of 300 nm diameter holes (period=400 nm, depth=130 nm), in 8×8 mm2 dies with overall feature dimensions of 120×120 mm2. Next, a negative volume image of the silicon surface structure was formed by distributing liquid UV curable polymer (Gelest) droplets between the silicon wafer and a flexible polyethylene terephthalate (PET) sheet. After curing by exposure to UV light, the molded structure was released from the wafer by peeling away the PET, resulting in a polymer replica of the silicon wafer structure adhered to the PET sheet. Then, 100 nm of $SiO_2$ was deposited over the polymer replica by electron beam evaporation, followed by deposition of a 200 nm silver thin film, also by electron beam evaporation, to complete the device. The separation distance for the nanodome array was 20 nm with the nanodome base diameter of 380 nm. The details of nanodome fabrication using nanoreplica molding process are shown in FIG. 10 and described above.

b. Flow Cell Incorporated with Nanodome Sensor (FIG. 8)

The flow cell of FIG. 8 was made with a stereolithography system (Viper SLA system, 3D Systems) using an optically clear resin (WaterClear Ultra 10122, DSM Somos). The dimensions of the flow chamber were 18.5×7.5×3 mm for length, width, and height, respectively. Inlet/outlet of the flow cell was 3×1 mm. Two cylindrical openings at the ends of the flow cell were tapped and screwed in with polypropylene barbed adapter (10-32 UNF×⅛" ID, Cole-Parmer) connected to tubing (⅛" ID×3/16" OD, TYGON R-3603). The nanodome surface was cut and attached as bottom surface of the flow cell using UV-cure adhesive (Addison Clear Wave). The top side of the flow cell was sealed by attaching a standard. No. 2 microscope slide cover glass functioning as a cover window using the same UV adhesive.

Detection Instrument

The Raman measurement was performed using a 785 nm wavelength diode laser system (Ocean Optics) coupled into an optical fiber 810 (FIG. 8). For detection of promethazine, the laser power was set to 100 mW. For detection of urea and urea/promethazine mixture, the laser was set to 150 mW. The laser was focused on the sensor surface by a 10× objective lens (NA=0.28). SERS photons were collected by the same objective lens, into a QE65000 spectrometer (Ocean Optics) using an integration time of 5 sec. for all experiments.

c. Experiment Procedures

Experimental procedures were identical for promethazine and urea as well as promethazine/urea mixture. For the concentrations series measurement, promethazine solution was prepared in DI water at 50, 25, 12.5, 6.25, 3.13, and 1.56 mg/mL. Urea solution was prepared in concentrations of 300, 150, 75, 37.5, 18.8, and 9.38 mM also in DI water. Urea and promethazine mixture was prepared in three different combinations: 300 mM, 25 mg/mL; 150 mM, 25 mg/mL; 300 mM, 12.5 mg/mL for urea and promethazine, respectively. Before the SERS measurement, 5 mL of analyte solution was pumped through the sensor tubing manually using a syringe and measurements were taken without flow. After the measurement, the flow cell was washed by emptying the analyte solution and flowing through 10 mL of DI water. Emptying and rinsing with DI water was repeated three times before introducing another analyte of with a different concentration. For statistical significance, measurements on the analyte concentration series were repeated five times (one measurement per analyte concentration in a series).

For the kinetic on/off measurements, the analyte sample and DI water were alternately pumped through the sensor tubing using a separate syringe pump (PHD 22/2000, Harvard Apparatus) for each solution at 60 sec. intervals. Tubing from the syringes containing the sample and blank solution were connected to a three-way stopcock valve which was used alternate the samples flowing into the sensor tubing. The solutions were pumped through the tubing at a flow rate of 5 mL/min. Although typical IV injection rates are significantly lower, a flow rate of 5 mL/min was chosen to facilitate the kinetic experiment and to minimize cross diffusion of analytes at the interface between different solutions as they are being pumped.

For comparison, urea detection was performed using a colorimetric urea assay kit (DIUR-500, BioAssay Systems). The same urea samples used for the experiment on nanodome sensor tubing were diluted 50-fold in DI water prior to the assay. 5 μL of urea sample for each concentration, standard urea solution (50 mg/dL) and DI water (blank) were transferred into wells of a clear bottom 96-well plate in triplicate. Then, 200 μL of assay reagent mixture included in the kit was added to the wells and incubated for 20 min at room temperature. After incubation, microplate reader (Synergy HT, BioTek Instruments) was used to measure the optical density of the samples at wavelength of 520 nm.

d. Data Analysis

The background of the raw SERS spectra was removed using 6th order polynomial fit, followed by signal filtering using Savitsky-Golay parameters with smooth window of 9 and polynomial order of 3. The processed spectra were then subtracted by the reference spectrum from the blank DI water to obtain the final spectra.

Figure 12:
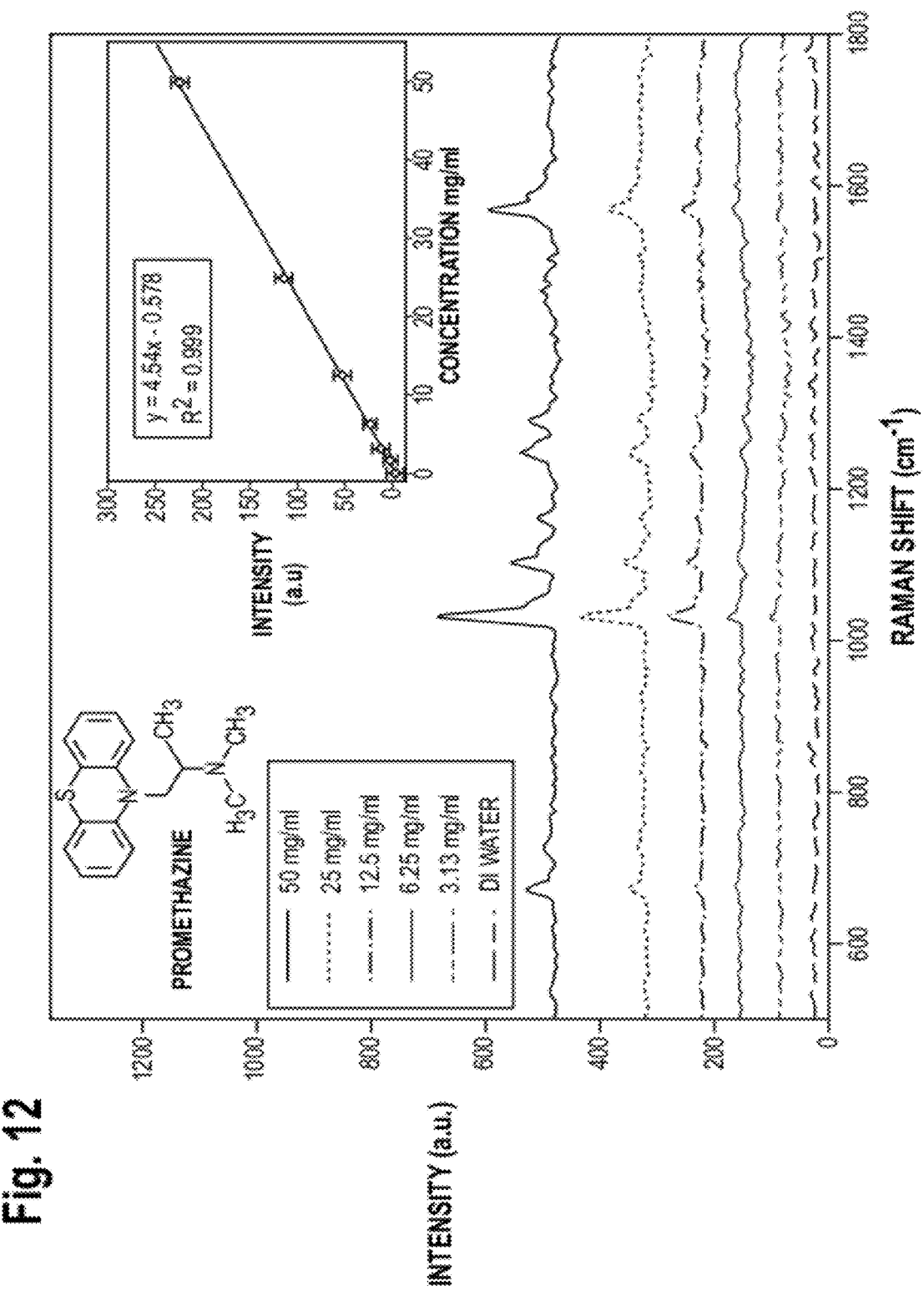
FIG. 12 is a plot of SERS spectra for promethazine solution within the sensor tubing. Primary Raman intensity peak for promethazine compound corresponding to the ring-breathing mode of the aromatic rings can be observed at 1030 cm-1. The inset shows Raman intensity measured at 1030 cm-1 as a function of promethazine concentration with error bars indicating ±1 standard deviation (N=5).

FIG. 12 compares the SERS spectra for promethazine solutions of varying concentrations ranging from 3.13 to 50 mg/mL, comprising the range of concentrations typically delivered to patients. The SERS spectra of promethazine solution exhibited a dominant Raman intensity peaks located at 1030 cm-1 due to the ring-breathing mode of the aromatic rings, and at 1567 cm-1 and 1589 cm-1 corresponding to aromatic C=C stretching modes of the molecule. Using the dominant peak located at 1030 cm-1 for analysis of promethazine, the inset shows the plot of the average Raman intensity as a function of promethazine concentration with error bars indicating ±1 standard deviation (N=5). A linear fit between the Raman intensity at 1030 cm-1 and the concentration of promethazine yielded an R2 value of 0.999. This demonstrates that the nanodome sensor tubing may be used to identify promethazine compound in solution and detect its concentration.

Figure 13:
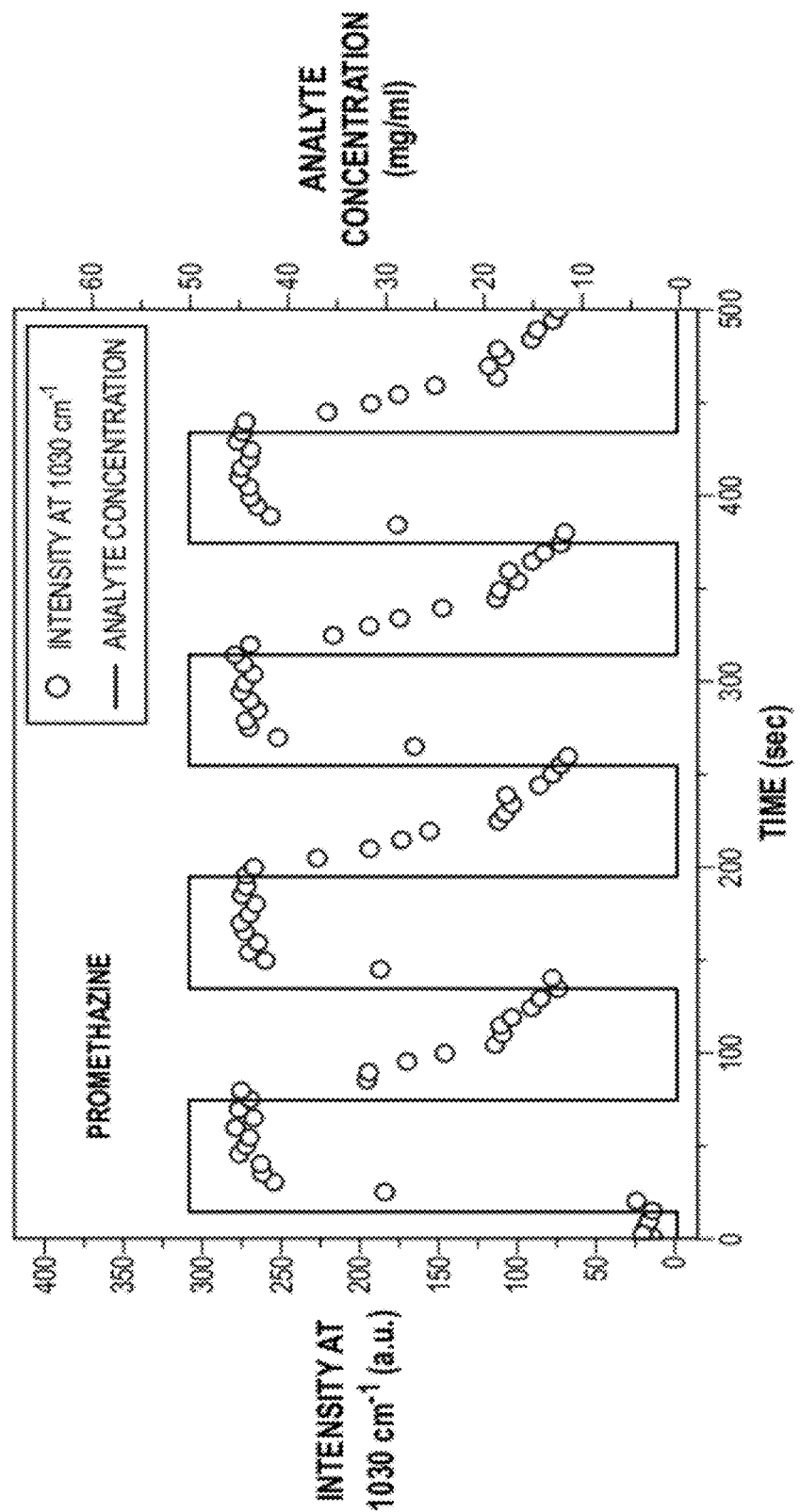
FIG. 13 is a kinetic plot of Raman intensity measured at 1030 cm-1 as 50 mg/mL promethazine solution and DI water were alternately pumped through the tubing at 60 sec. intervals.

In order to investigate the real-time detection capability of the nanodome sensor, SERS measurement was made with 50 mg/mL promethazine solution and DI water alternately pumped through the tubing at 60 sec. intervals. Measurements were taken every 5 sec. which was same as the integration time for the CCD in the spectrometer. FIG. 13 shows the kinetic plot of Raman intensity measured at 1030 cm-1 as a function of time. The results indicate that real-time monitoring of solution flowing through tubing can be achieved for the nanodome sensors. Delay in sensor response can be observed due to analyte molecules diffusing across a stagnant flow layer that forms near the surface of the nanodome sensor as solutions are pumped through the flow cell. Considering the typical injection rate used to administer drugs, the delay in sensor response due to diffusion in the stagnant fluid layer should not cause hindrance in detecting medication error before any serious health hazard is posed.

From the kinetic plot, the standard deviation (σ) of the Raman signal measured at 1030 cm-1 was 3.51. Based on the linear dose response curve (inset of FIG. 12) and setting sensor readout resolution as three standard deviations (3σ), the limit of detection for nanodome sensors on promethazine was 2.32 mg/mL. The results suggest that nanodome sensor tubing system is capable of identifying promethazine compounds and detecting concentrations that are clinically relevant. The system could be used detect and prevent hazard associated with IV-delivered promethazine over the maximum allowed concentration of 25 mg/mL.

Figure 14:
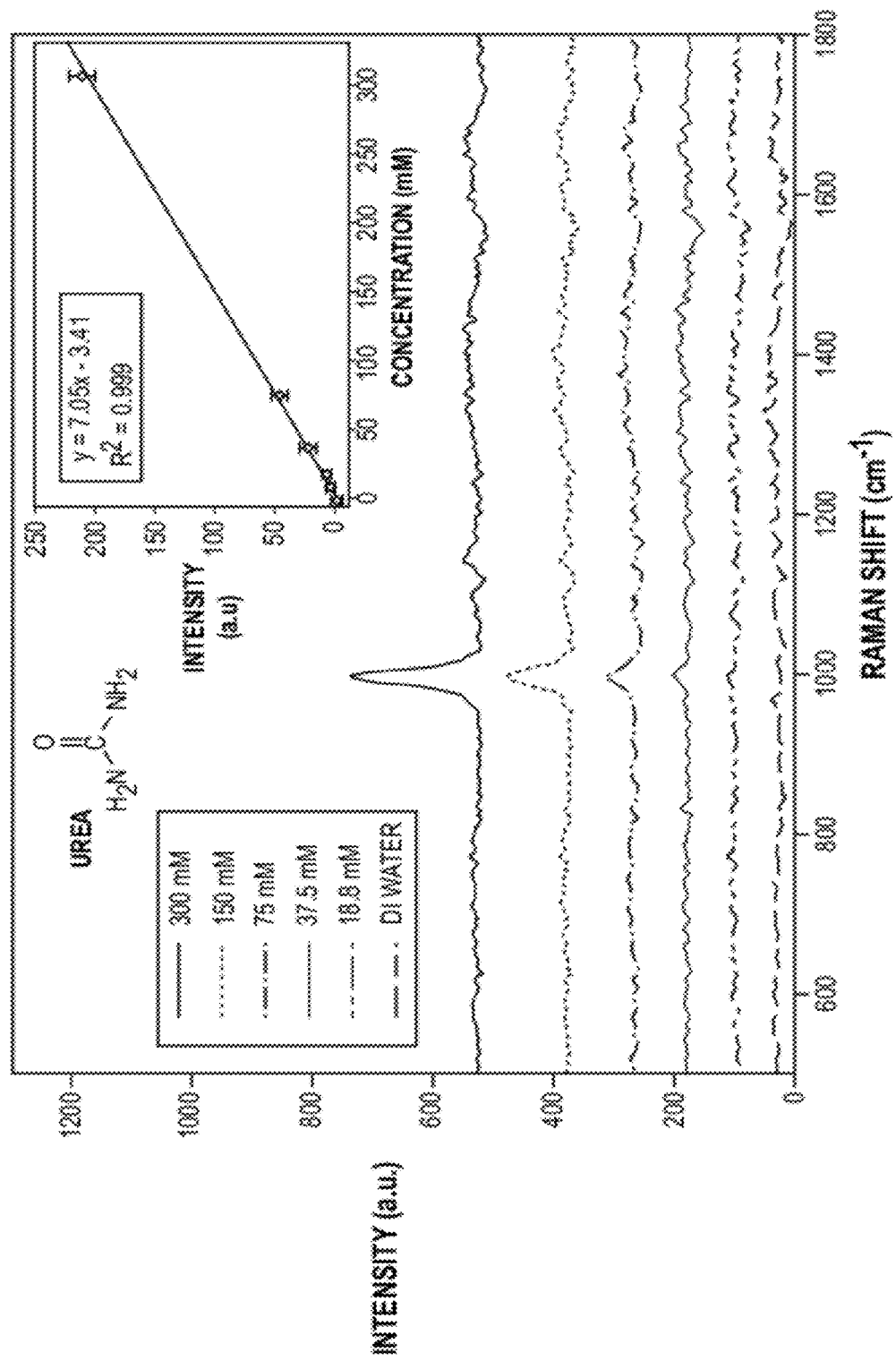
FIG. 14 compares the SERS spectra for urea solutions of varying concentrations ranging from 18.8 to 300 mM, encompassing the range of urea concentration typically measured clinically. Urea solution exhibited a primary Raman intensity peak at 1000 cm-1 from the symmetrical C—N stretch. The inset shows the plot of the average Raman intensity measured at 1000 cm-1 as a function of promethazine concentration with error bars indicating ±1 standard deviation (N=5).

FIG. 13 is kinetic plot of Raman intensity measured at 1030 cm-1 as 50 mg/mL promethazine solution and DI water were alternately pumped through the tubing at 60 sec. intervals e. Detection of Urea As with promethazine solution, similar measurements were made for the detection of urea solution in tubing. FIG. 14 compares the SERS spectra for urea solutions of varying concentrations ranging from 18.8 to 300 mM, encompassing the range of urea concentration typically measured clinically. Urea solution exhibited a primary Raman intensity peak at 1000 cm-1 from the symmetrical C—N stretch. The inset of FIG. 14 shows the plot of the average Raman intensity measured at 1000 cm-1 as a function of promethazine concentration with error bars indicating ±1 standard deviation (N=5). The linear fit with R2 value of 0.999 was obtained. Again, this demonstrates that the nanodome sensor tubing may be used to identify urea compound in solution and detect its concentration.

Raman intensity peak for urea corresponding to the symmetrical C—N stretch can be observed at 1000 cm-1. Inset: Raman intensity measured at 1000 cm-1 as a function of urea concentration with error bars indicating ±1 standard deviation (N=5).

Figure 15:
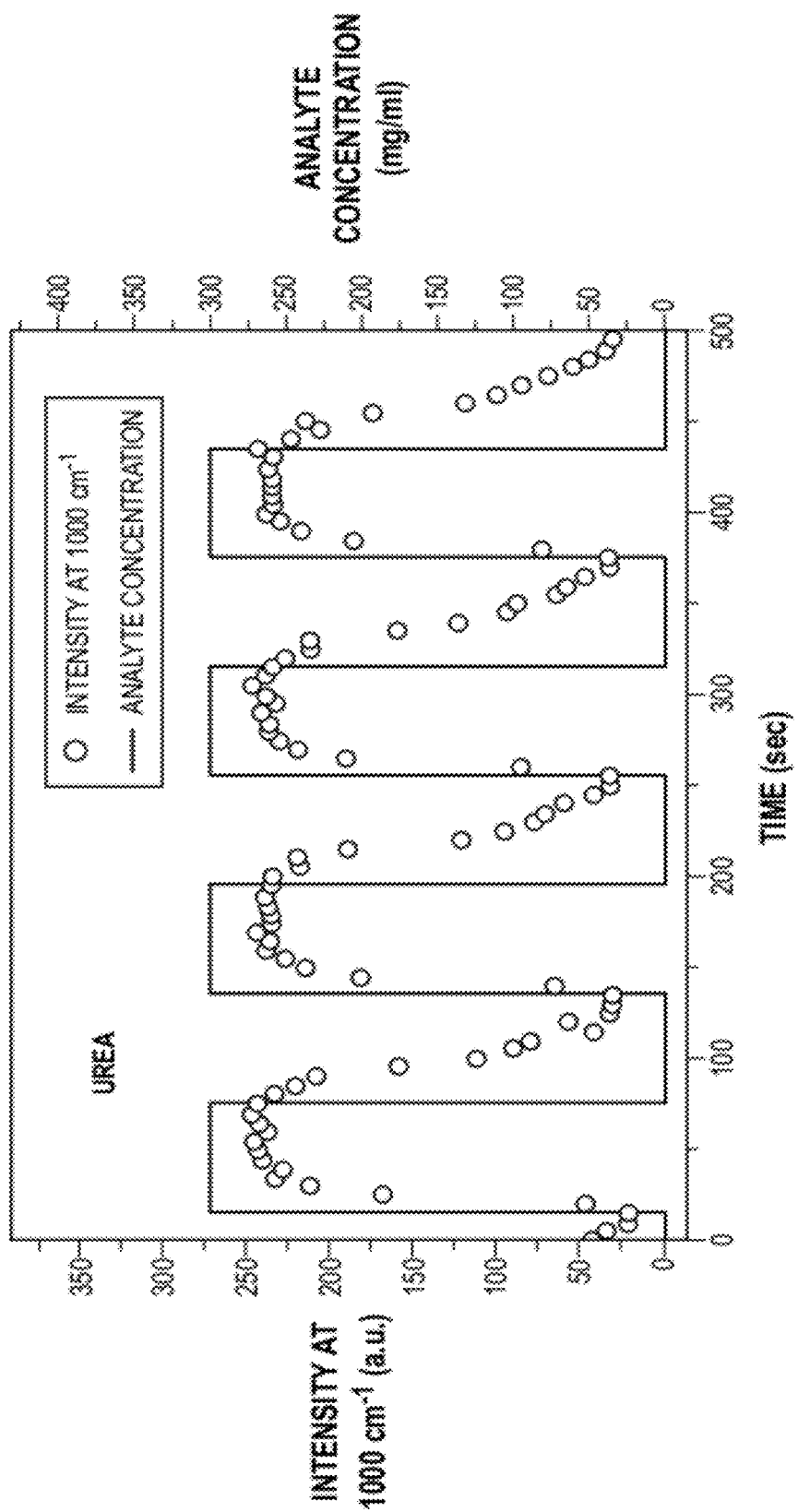
FIG. 15 is a kinetic plot of Raman intensity measured at 1000 cm-1 as 300 mM urea solution and DI water were alternately pumped through the tubing at 60 sec. intervals.

To investigate the real-time detection capability for urea, SERS measurement was made with 300 mM urea solution and DI water alternately pumped through the tubing at 60 sec. intervals. Same integration time and measurement interval as with promethazine experiment was used. FIG. 15 shows the kinetic plot of Raman intensity measured at 1000 cm-1 as a function of time. Delay in sensor response was observed for the urea measurement as well, but it should not cause issues for real-time detection.

For urea, the standard deviation (σ) for the Raman intensity at 1000 cm-1 was 2.54. Based on the linear dose response curve (inset of FIG. 14) and three standard deviation (3σ) threshold for the sensor readout resolution, the limit of detection for nanodome sensors on urea was 10.8 mM. The results suggest that nanodome sensor tubing system is capable of monitoring kidney activity of a patient through identifying and detecting urea well below the typical concentration in urine. The system could also be used to monitor renal clearance failure by detecting urea concentration in blood or dialysate since the detection limit of the system is below the pathophysiological concentration of 30-150 mM.

f. Detection of Urea/Promethazine Mixture

Figure 16:
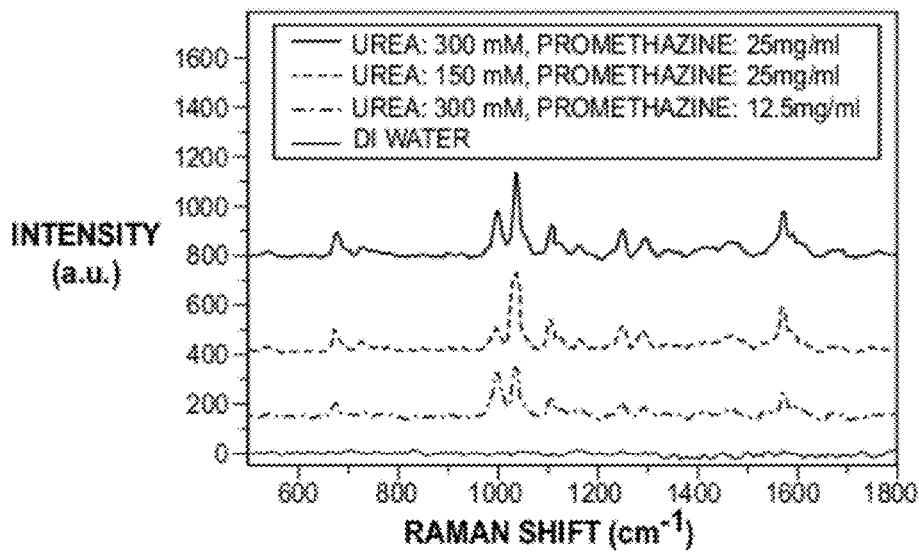
FIG. 16 is a plot of SERS spectra for the urea and promethazine mixtures, where primary Raman intensity peaks for both urea and promethazine can be observed at 1000 cm-1 and 1030 cm-1, respectively. The intensity values for each analyte were consistent with measurements made with single analyte solution.

The ability for multiplexed detection of analytes is useful as multiples drugs or nutrients are often delivered to patients through IV lines in clinical settings. One advantage of SERS-based sensors is its capability for detection of multiple analytes simultaneously when the Raman scattered peaks can be individually distinguished. To demonstrate the multiplexed detection capability of the SERS nanodome sensor, a mixture of urea and promethazine at varying concentrations were introduced to the sensor tubing. FIG. 16 shows the SERS spectra for the urea and promethazine mixtures where primary Raman intensity peaks for both urea and promethazine can be observed at 1000 cm-1 and 1030 cm-1, respectively. The intensity values for each analyte were consistent with measurements made with single analyte solution.

In this example, we have demonstrated a SERS nanodome sensor incorporated in a flow cell for real-time biochemical sensing of fluid within tubing. We have successfully performed a proof-of-concept experiment on the label-free detection of urea and promethazine compounds within the sensor incorporated tubing. Through the experiment, we have demonstrated the potential for in-line nanodome sensor detection system that would allow real-time detection of fluid samples from patients without taking samples and performing laboratory based tests. The technology could also be used to identify drug compounds that are being administered to patients for enhanced safety for smart infusion system. Nanoreplica molding method that was used to make the nanodome substrates is a low-cost, mass-manufacturing process which would allow the devices to be commercialized and adopted in clinical setting as disposable single use sensors. We plan to further test this approach by detection of additional metabolites and by detection of urinary metabolites within urine samples, rather than in buffer as demonstrated in this work. We also plan to investigate the potential to develop the nanodome sensors that are highly flexible so that it may be attached to curved surfaces which would further open up opportunities for biochemical detection. For example, the sensor could be placed onto the internal surface of the tubing or containers for wide range of applications including but not limited to medical, food processing, and environmental monitoring.

6. Instrumentation

DFB Laser Biosensor

The DFB laser biosensor detection instrument for a biosensor in tubing 500 is shown schematically in FIG. 5. The instrument is comprised of a pulsed laser excitation source 502, coupled to an optical fiber 504A through a beam splitter 506, which illuminates the sensor 510 structures through a lens 508. The laser emission is gathered into the same fiber 504A, which guides the light through a filter 512 (to remove the excitation wavelength) to a high resolution spectrometer 514. While a conventional optical-bench scale Nd:Yag pulsed laser was used to provide the optical pumping necessary to produce lasing of our initial DFB biosensor, for a compact system, we plan to incorporate a microchip Nd:Yag laser into the proposed system. Such a laser has sufficient energy and pulse width for excitation of plastic-based DFB lasers. An exemplary laser is a JDS Uniphase PowerChip NanoLaser, which is a diode-pumped passively Q-switched solid state dye laser that can produce high peak power with repetition rates in the 100-1000 Hz range at the wavelength required for Rhodamine excitation. The size of the laser is ~300×100×100 $mm^3$, representing the largest component of the detection system. The laser would meet the excitation energy and pulse-width requirements of DFB laser biosensors. Smaller Nd:Yag microchip lasers have recently become commercially available, such as an Arctic Photonics product that offers 0.1-10 ns pulses of ~600 nm wavelength light, with pulse energy up to 200 µJ. (<10 µJ is needed for the DFB lasing threshold). Unlike the JDS Uniphase product, the Arctic Photonics laser is a custom configuration, but with a greatly reduced size (44×30×30 $mm^3$) that will be suitable for a miniature detection system. The spectrometer 514 can be a compact Ocean Optics HR4000. The distal end of the excitation/collection fiber lens assembly will be held by a linear translation stage 520 that can move in eight 3 mm increments down the length of the tubing to probe individual sensor locations.

PC-SERS

As shown in FIG. 5, the PC-SERS detection instrument is substantially similar to the DFB instrument, but utilizes a CW laser 560 (200 mW, λ=785 nm) and a second Ocean Optics HQE65000 miniature spectrometer 562 centered at 785 nm. The fiber/lens assembly 564 will not require a motion stage, although the holding fixture 566 will enable small adjustments in illumination angle to be made in the direction perpendicular to the sensor 552 PC grating lines, using set screws. The laser illumination will be polarized perpendicular to the PC grating lines for TM mode excitation, or parallel to the grating lines for TE mode excitation.

A holding fixture 546 and alignment housing 522 is designed and fabricated for interfacing the detection fibers accurately with the sensor tubing 500, and providing a rigid mechanical platform for mounting the fibers and linear translation stage. The alignment collars 524 on the tubing will ensure that the sensor locations are illuminated in the desired locations in the up/downstream direction.

For photonic crystal sensor incorporated into tubing, the illumination and detection arrangements of the previously cited patent literature can be used. For example, a white light source or LED light can illuminate the clear plastic or glass tubing with the sensor formed therein and the reflected light directed to a spectrometer to measure the shift in peak wavelength of the reflected light due to binding interactions on the sensor surface. Holding fixtures or the like can be used to precisely position the illuminating and detection fibers of the detection instrument relative to the PC sensor areas in the tubing. The PC sensor areas in the tubing can be coated with capture molecules to capture analytes of interest present in the tubing.

7. Conclusion

Numerous examples of biosensors incorporated into tubing and related methods for manufacturing and detection instrumentation have been described. Variations from the details of the illustrated embodiments are of course possible without departure from the scope of the claims.

In one aspect, a biosensor has been described comprising a tube and a photonic sensor fabricated on a flexible plastic film in fluid communication with the contents of the tube, e.g., wrapped around an existing tube with a whole in the tube, or with the photonic sensor part of the tube itself as shown in FIG. 5. The photonic sensor can take the form of a photonic crystal biosensor, a distributed feedback (DFB) laser biosensor, and a Surface Enhanced Raman Spectroscopy (SERS) biosensor, e.g., a PC-SERS or a PC-SERS nanodome sensor.

In still another aspect, the invention can take the form of a urinary catheter having a photonic sensor fabricated on a flexible plastic film in fluid communication with the interior of the catheter.

In still another aspect, the invention can take the form of a blood tubing set having a photonic sensor fabricated on a flexible plastic film in fluid communication with the interior of the blood tubing set.

In yet another aspect, the invention can take the form of an infusion arrangement comprising a source of liquid containing a drug for administration to a patient, a tube connecting the source to the patient either directly or indirectly, and a photonic sensor fabricated on a flexible plastic film in fluid communication with the interior of the tube.

In still another aspect, a method of noninvasive, continuous in-line monitoring of the components of bodily fluids, such as blood and urine, has been disclosed comprising the steps of: flowing the bodily fluids through a tube having a photonic biosensor in fluid communication with the bodily fluids, and interrogating the biosensor with a detection instrument positioned exterior of the tubing to thereby measure interactions between the biosensor and components of the bodily fluids.

We claim:

1. A Surface Enhanced Raman Spectroscopy (SERS) biosensor, comprising:
    an array of closely-spaced metal nanodomes fabricated on a flexible plastic film, wherein the metal nanodomes comprise a periodic grating structure formed in a polymer on the flexible plastic film substrate, a dielectric material deposited on the periodic grating structure in the polymer to provide a periodic array of domes, and a metal thin film coating deposited on the dielectric material.

2. The biosensor of claim 1, wherein the metal thin film coating comprises a coating of silver.

3. The biosensor of claim 1, further comprising a detection instrument having a laser for interrogating the biosensor and a spectrometer, and wherein the spacing between the metal nanodomes and the periodicity of the metal nanodomes in the array is such that a resonance is created near to or at the wavelength of the laser of the detection instrument.

4. The biosensor of claim 1, wherein the SERS nanodome sensor is incorporated into a sample testing device selected from the group of sample testing devices consisting of:
    a) a tube, the biosensor placed in fluid communication with the contents of the tube;
    b) a liquid-containing vessel, the biosensor placed in fluid communication with the contents of the vessel;
    c) a glass slide;
    d) a test tube; and
    e) a flow cell.

5. A biosensor detection arrangement comprising:
    a) SERS nanodome sensor according to claim 1;
    b) a detection instrument including a laser illumination source and a spectrometer; and
    c) a holding fixture for holding the SERS nanodome sensor relative to the detection instrument.

6. The biosensor detection arrangement of claim 5, wherein the SERS nanodome sensor is incorporated into a section of tubing such that the SERS nanodome sensor is placed in fluid communication with the contents of the tubing, and wherein the holding fixture provides for relative movement between components of the detection system and the section of tubing.

7. The biosensor detection arrangement of claim 6, wherein the SERS nanodome sensor is incorporated into a flow cell.

8. The biosensor of claim 1, wherein the nanodomes after depositing of the thin film metal coating have a separation distance of between 10 and 30 nm.

9. The biosensor of claim 1, wherein the dielectric material is silicon dioxide ($SiO_2$).

10. A method of manufacturing a Surface Enhanced Raman Spectroscopy (SERS) nanodome sensor, comprising the steps of:
   providing a flexible plastic substrate with a layer of ultraviolet-curable polymer thereon;
   curing the ultraviolet-curable polymer on the substrate to a solid state while in contact with a mold template to form a two-dimensional periodic grating structure on the substrate;
   depositing a dielectric material on the two-dimensional periodic grating structure to thereby form a two-dimensional periodic array of nanodomes on the substrate; and
   depositing a thin film metal layer on the dielectric material forming the two-dimensional periodic array of nanodomes.

11. The method of claim 10, further comprising the step of removing a section of the flexible plastic substrate having the two-dimensional periodic array of nanodomes and the thin-film metal layer deposited thereon, and incorporating the section into a sample testing device.

12. The method of claim 11, wherein the sample testing device is selected from the group of sample testing devices consisting of:
   a) a tube, the biosensor placed in fluid communication with the contents of the tube;
   b) a liquid-containing vessel, the biosensor placed in fluid communication with the contents of the vessel;
   c) a glass slide;
   d) a test tube; and
   e) a flow cell.

13. The method of claim 11, wherein the nanodomes after depositing of the thin film metal coating have a separation distance of between 10 and 30 nm.

14. The method of claim 10, wherein the dielectric material is silicon dioxide ($SiO_2$).

15. A biosensor comprising the combination of a Surface Enhanced Raman Spectroscopy (SERS) nanodome biosensor comprising an array of closely-spaced metal nanodomes and a distributed feedback laser biosensor, and
   a tube or flow cell incorporating the combination of the (SERS) nanodome biosensor and the distributed feedback laser biosensor;
   wherein the SERS nanodome biosensor and the distributed feedback laser biosensor are formed on a flexible plastic film and arranged in a spaced apart arrangement; and
   wherein a first region of the flexible plastic film contains the SERS nanodome biosensor and a second region of the flexible plastic film contains the distributed feedback laser biosensor.

16. The biosensor of claim 15, wherein the flexible plastic film comprises a plurality of separate, spaced apart distributed feedback laser biosensor regions.

* * * * *